United States Patent
Yamazaki

(10) Patent No.: US 10,729,892 B2
(45) Date of Patent: Aug. 4, 2020

(54) MEDICAL ELONGATED BODY

(71) Applicant: TERUMO KABUSHIKI KAISHA, Shibuya-ku, Tokyo (JP)

(72) Inventor: Ryosuke Yamazaki, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 220 days.

(21) Appl. No.: 15/939,845

(22) Filed: Mar. 29, 2018

(65) Prior Publication Data

US 2018/0280666 A1 Oct. 4, 2018

(30) Foreign Application Priority Data

Mar. 31, 2017 (JP) ................. 2017-071995

(51) Int. Cl.
| | | |
|---|---|---|
| *A61M 25/10* | (2013.01) | |
| *A61B 17/12* | (2006.01) | |
| *A61M 29/02* | (2006.01) | |
| *A61B 17/22* | (2006.01) | |

(Continued)

(52) U.S. Cl.
CPC ... *A61M 25/1002* (2013.01); *A61B 17/12109* (2013.01); *A61B 17/12136* (2013.01); *A61M 29/02* (2013.01); *A61B 17/320725* (2013.01); *A61B 2017/22001* (2013.01); *A61M 25/104* (2013.01); *A61M 2025/0183* (2013.01); *A61M 2025/1004* (2013.01); *A61M 2025/109* (2013.01); *A61M 2025/1075* (2013.01);
(Continued)

(58) Field of Classification Search
CPC .... A61M 2025/1086; A61M 2025/109; A61M 2025/1075; A61M 2025/1085; A61M 2025/1004; A61M 2025/1088; A61M 25/104; A61M 25/1006; A61B 17/3207; A61B 17/320725; A61B 17/22032
See application file for complete search history.

(56) References Cited

U.S. PATENT DOCUMENTS

| | | | | |
|---|---|---|---|---|
| 5,176,693 A | * | 1/1993 | Pannek, Jr. | .... A61B 17/320725 604/22 |
| 5,320,634 A | * | 6/1994 | Vigil | .............. A61B 17/320725 604/103.08 |

(Continued)

FOREIGN PATENT DOCUMENTS

JP         2009-112361 A         5/2009

*Primary Examiner* — Eric J Rosen
*Assistant Examiner* — Mohammed S Adam
(74) *Attorney, Agent, or Firm* — Buchanan Ingersoll & Rooney PC

(57) ABSTRACT

A medical elongated body is disclosed, which is able to make a nick in a stenosed site and is capable of preferably widening the stenosed site in which the nick is made. A balloon catheter is disclosed, which includes a shaft, a dilation member that is fixed to the shaft on a distal side, and an elastic member that is disposed on an inner surface of the dilation member. The dilation member includes a projection portion, which is a part of the dilation member protruding in a radial direction due to the elastic member disposed at a position where the inner surfaces of the dilation member face each other. A material of the elastic member is configured to be a material, which is further stretched than a material of the dilation member in a circumferential direction when the dilation member dilates.

18 Claims, 12 Drawing Sheets

(51) Int. Cl.
  *A61M 25/01* (2006.01)
  *A61B 17/3207* (2006.01)
(52) U.S. Cl.
  CPC ............ *A61M 2025/1084* (2013.01); *A61M 2025/1086* (2013.01); *A61M 2205/0216* (2013.01)

(56) References Cited

U.S. PATENT DOCUMENTS

| | | | | |
|---|---|---|---|---|
| 5,616,149 A * | 4/1997 | Barath | ........... | A61B 17/320725 604/103.07 |
| 5,766,203 A * | 6/1998 | Imran | ............. | A61F 2/958 604/103.05 |
| 6,613,066 B1 * | 9/2003 | Fukaya | ............. | A61M 25/1034 606/192 |
| 6,896,842 B1 * | 5/2005 | Hamilton | ............. | A61L 29/049 264/515 |
| 6,960,186 B1 * | 11/2005 | Fukaya | ............. | A61M 25/1027 604/102.02 |
| 7,780,626 B2 * | 8/2010 | Wu | ................. | A61B 17/320725 604/523 |
| 7,799,043 B2 * | 9/2010 | O'Brien | ......... | A61B 17/320725 606/159 |
| 8,211,354 B2 * | 7/2012 | Burton | ........... | A61B 17/320725 264/532 |
| 8,764,705 B2 * | 7/2014 | Hennessey | ..... | A61B 17/320725 264/523 |
| 9,192,747 B2 * | 11/2015 | Hardert | ............... | A61M 25/104 |
| 9,226,768 B2 * | 1/2016 | Gunderson | .... | A61B 17/320725 |
| 9,242,076 B2 * | 1/2016 | Burton | ........... | A61B 17/320725 |
| 9,302,071 B2 * | 4/2016 | Manderfeld | ... | A61B 17/320725 |
| 9,302,079 B2 * | 4/2016 | Burton | ............. | A61M 25/1002 |
| 9,339,291 B2 * | 5/2016 | Aggerholm | .... | A61B 17/320725 |
| 9,592,369 B2 * | 3/2017 | Yamaguchi | ........... | A61L 29/085 |
| 9,604,036 B2 * | 3/2017 | Burton | ................. | A61M 25/10 |
| RE46,581 E * | 10/2017 | Lafontaine | | |
| 10,182,841 B1 * | 1/2019 | Rousu | ................ | A61M 25/104 |
| 10,286,190 B2 * | 5/2019 | Moelgaard-Nielsen | ..................... | A61M 25/10 |
| 2002/0082635 A1 * | 6/2002 | Kammerer | ........ | A61M 25/1002 606/193 |
| 2004/0034384 A1 * | 2/2004 | Fukaya | ................ | A61M 25/104 606/191 |
| 2004/0133223 A1 * | 7/2004 | Weber | ............ | A61B 17/320725 606/159 |
| 2004/0193196 A1 * | 9/2004 | Appling | ......... | A61B 17/320725 606/167 |
| 2005/0137618 A1 * | 6/2005 | Kunis | ................ | A61B 17/22 606/192 |
| 2005/0288629 A1 * | 12/2005 | Kunis | ................ | A61M 25/104 604/96.01 |
| 2006/0173487 A1 * | 8/2006 | Uflacker | ........ | A61B 17/320725 606/198 |
| 2007/0088380 A1 * | 4/2007 | Hirszowicz | ........ | A61M 25/1006 606/194 |
| 2007/0244501 A1 * | 10/2007 | Horn | ................... | A61L 29/085 606/194 |
| 2008/0249464 A1 * | 10/2008 | Spencer | ........... | A61M 25/1002 604/103 |
| 2009/0171278 A1 * | 7/2009 | Hirszowicz | ........ | A61M 25/1006 604/97.01 |
| 2009/0171284 A1 * | 7/2009 | Burke | ................ | A61M 25/104 604/104 |
| 2009/0247945 A1 * | 10/2009 | Levit | ................ | A61M 25/1006 604/103 |
| 2009/0270801 A1 * | 10/2009 | Shimada | ........... | A61M 25/0023 604/96.01 |
| 2010/0042198 A1 * | 2/2010 | Burton | ................... | A61F 2/958 623/1.11 |
| 2010/0174235 A1 * | 7/2010 | Yamaguchi | ........... | A61L 29/085 604/103.08 |
| 2012/0130408 A1 * | 5/2012 | Schur | ............ | A61B 17/320725 606/159 |
| 2012/0245608 A1 * | 9/2012 | Hirszowicz | ........ | A61M 25/1006 606/159 |
| 2013/0096604 A1 * | 4/2013 | Hanson | ................ | A61M 25/104 606/194 |
| 2013/0116655 A1 * | 5/2013 | Bacino | ............. | A61M 25/1002 604/509 |
| 2013/0226131 A1 * | 8/2013 | Bacino | ................. | A61L 29/146 604/500 |
| 2014/0100592 A1 * | 4/2014 | Burton | ............. | A61M 25/1038 606/159 |
| 2014/0114325 A1 * | 4/2014 | Wu | ................ | A61B 17/320725 606/127 |
| 2014/0142598 A1 * | 5/2014 | Fulton, III | ..... | A61B 17/320725 606/159 |
| 2014/0163593 A1 * | 6/2014 | Schur | ............. | A61B 17/320725 606/159 |
| 2014/0296889 A1 * | 10/2014 | Avneri | ............ | A61B 17/32037 606/159 |
| 2014/0324079 A1 * | 10/2014 | Silvestro | .......... | A61B 17/32075 606/159 |
| 2015/0088186 A1 * | 3/2015 | Shimogami | ......... | A61M 25/104 606/194 |
| 2015/0127034 A1 * | 5/2015 | Eaton | ............. | A61B 17/320758 606/159 |
| 2015/0141917 A1 * | 5/2015 | Tilson | ................... | A61F 2/2433 604/103.07 |
| 2016/0095619 A1 * | 4/2016 | McMahon | ..... | A61B 17/320725 606/159 |
| 2016/0128718 A1 * | 5/2016 | Aggerholm | ............. | A61L 29/06 606/159 |
| 2016/0262789 A1 * | 9/2016 | Root | ............ | A61B 17/320725 |
| 2017/0105758 A1 * | 4/2017 | Piccagli | ......... | A61B 17/320725 |
| 2017/0128703 A1 * | 5/2017 | Elgaard Pederson | ........................ | A61M 25/1002 |
| 2017/0273697 A1 * | 9/2017 | Enami | ................... | A61M 29/02 |
| 2017/0319231 A1 * | 11/2017 | Nishigishi | ...... | A61B 17/320725 |
| 2018/0280666 A1 * | 10/2018 | Yamazaki | ......... | A61M 25/1002 |
| 2019/0344054 A1 * | 11/2019 | Slattery | .......... | A61B 17/320725 |

\* cited by examiner

P1

P2

P3

MEDICAL ELONGATED BODY

CROSS-REFERENCES TO RELATED APPLICATIONS

This application claims priority to Japanese Application No. 2017-071995 filed on Mar. 31, 2017, the entire content of which is incorporated herein by reference.

TECHNICAL FIELD

The present disclosure relates to a medical elongated body including a dilation member, which is capable of dilating in a biological lumen.

BACKGROUND ART

A balloon catheter (medical elongated body) is known as a medical instrument, which is used in a technique for widening a lesion area (stenosed site) formed in a biological lumen such as a blood vessel. The balloon catheter has a shaft and a balloon (dilation member) that is fixed to the shaft on a distal side.

The balloon fixed to the shaft on the distal side can be introduced into a biological lumen through a puncture site via an introducer sheath, a guiding catheter, or the like and is delivered to a lesion area. The balloon delivered to the lesion area dilates in a state of being disposed in the lesion area and applies a dilation pressure to the lesion area.

Recently, as a type of balloon catheter, a balloon catheter, in which a blade-like element formed of a resin having relatively high rigidity, a metal, or the like is attached to a balloon on an outer surface side, has been proposed (for example, refer to JP-A-2009-112361). In the balloon catheter, the balloon disposed in a lesion area dilates so that the lesion area can be widened while the element attached to the balloon on the outer surface side makes a nick in the lesion area. Therefore, the balloon catheter exhibits a particularly high therapeutic effect on widening a highly-calcified lesion (hardened lesion area due to calcification).

However, in the balloon catheter described above, since an element is attached to a balloon on an outer surface side, although the element can make a nick in a lesion area, it can be difficult to cause a dilation pressure of the balloon to evenly act on the lesion area in which the nick is made.

In order to preferably widen a lesion area in which a nick is made, a practitioner needs to perform a technique as follows. That is, a practitioner needs to make a nick in a stenosed site to a certain extent using the balloon catheter to which the element is attached. Thereafter, the practitioner needs to replace the balloon catheter with a balloon catheter to which no element is attached and to widen the stenosed site in which the nick is made. In the technique, a practitioner needs to separately use the balloon catheter to which the element is attached and a balloon catheter to which no element is attached, so that the technique becomes troublesome and economic efficiency in medical treatment deteriorates.

SUMMARY

In accordance with an exemplary embodiment, a medical elongated body is disclosed, which is able to make a nick in a stenosed site and is capable of preferably widening the stenosed site in which the nick is made.

In accordance with an exemplary embodiment, a medical elongated body is disclosed, which includes a shaft, a dilation member that is fixed to the shaft on a distal side, and an elastic member that is disposed on an inner surface of the dilation member. The dilation member includes a projection portion, which is a part of the dilation member protruding in a radial direction due to the elastic member disposed at a position where the inner surfaces of the dilation member face each other. A material of the elastic member is configured to be a material, which is further stretched than a material of the dilation member in a circumferential direction when the dilation member dilates. When the dilation member dilates under a first internal pressure, a first lumen is formed inside the dilation member, and the projection portion is formed on an outer surface of the dilation member. When the dilation member dilates under a second internal pressure higher than the first internal pressure, the elastic member is stretched in the circumferential direction, and the adhered inner surfaces of the dilation member are separated from each other due to the elastic member such that the projection portion is not formed on the outer surface of the dilation member, so that a second lumen greater than the first lumen is formed. When the dilation member is reduced in pressure to a third internal pressure lower than the second internal pressure, stretching of the elastic member in the circumferential direction is canceled, so that a third lumen smaller than the second lumen is formed and the projection portion is formed again on the outer surface of the dilation member.

In accordance with an exemplary embodiment, when the dilation member dilates under the first internal pressure, the projection portion is formed on the outer surface of the dilation member. Accordingly, the medical elongated body of the present disclosure can make a nick in a stenosed site due to the dilation member, which dilates under the first internal pressure. In the medical elongated body of the present disclosure, when the dilation member dilates under a pressure shifted from the first internal pressure to the second internal pressure, the projection portion on the outer surface of the dilation member becomes small or the projection portion disappears from the outer surface of the dilation member, and an outer diameter of the dilation member increases. Accordingly, the medical elongated body of the present disclosure can cause a dilation pressure of a balloon to evenly act on a stenosed site in which a nick is made. Therefore, the medical elongated body of the present disclosure can make a nick in a stenosed site and can preferably widen the stenosed site in which the nick is made.

In accordance with an exemplary embodiment, a medical elongated body is disclosed, comprising: a shaft; a dilation member configured to be fixed to the shaft on a distal side; and an elastic member configured to be disposed on an inner surface of the dilation member, wherein the dilation member includes a projection portion which is a part of the dilation member protruding in a radial direction due to the elastic member disposed at a position where the inner surfaces of the dilation member face each other, wherein the elastic member is formed of a material which is further stretched than a material of the dilation member in a circumferential direction when the dilation member dilates, and a rigidity member having rigidity higher than rigidity of the dilation member and the elastic member, wherein the rigidity member has an elliptical cross-sectional shape perpendicular to an axis of the shaft, wherein when the dilation member dilates under a first internal pressure, a first lumen is formed inside the dilation member, and the projection portion is formed on an outer surface of the dilation member, wherein when the dilation member dilates under a second internal pressure higher than the first internal pressure, the elastic member is stretched in the circumferential direction, and the adhered inner surfaces of the dilation member are separated from each other due to the elastic member such that the projection portion is not formed on the outer surface of the dilation member, so that a second lumen greater than the first lumen is formed, and wherein when the dilation member is reduced in pressure to a third internal pressure lower than the second internal pressure, stretching of the elastic member in the circumferential direction is canceled, so that a third lumen smaller than the second lumen is formed and the projection portion is formed again on the outer surface of the dilation member.

In accordance with an exemplary embodiment, a medical elongated body is disclosed, comprising: a shaft; a dilation member configured to be fixed to the shaft on a distal side; and a plurality of elastic members configured to be disposed on an inner surface of the dilation member, wherein the dilation member includes a plurality of projection portions which are a part of the dilation member protruding in a radial direction due to the plurality of elastic members disposed at positions where the inner surfaces of the dilation member face each other, wherein a material of the plurality of elastic members is configured to be a material which is further stretched than a material of the dilation member in a circumferential direction when the dilation member dilates, wherein when the dilation member dilates under a first internal pressure, a first lumen is formed inside the dilation member, and the plurality of projection portions are formed separately at equal intervals in the circumferential direction on an outer surface of the dilation member, wherein when the dilation member dilates under a second internal pressure higher than the first internal pressure, the plurality of elastic members are stretched in the circumferential direction, and the adhered inner surfaces of the dilation member are separated from each other due to the plurality of elastic members such that the projection portions are not formed on the outer surface of the dilation member, so that a second lumen greater than the first lumen is formed, and wherein when the dilation member is reduced in pressure to a third internal pressure lower than the second internal pressure, stretching of the plurality of elastic members in the circumferential direction is canceled, so that a third lumen smaller than the second lumen is formed and the projection portions are formed again on the outer surface of the dilation member.

DETAILED DESCRIPTION

Hereinafter, with reference to the drawings, embodiments of the present disclosure will be described. Note that, for the convenience of description, there are cases where the dimensional ratios of the drawings are exaggerated and are different from the actual ratios.

FIGS. 1A to 5B are views illustrating a configuration of each portion of a balloon catheter 1 according to Embodiment 1 (corresponding to a medical elongated body).

The balloon catheter 1 according to the present embodiment is configured to be a medical instrument in which a shaft 10 is inserted through a biological lumen V and a balloon 20 disposed in the shaft 10 on a distal side dilates in a stenosed site N (lesion area), so that the stenosed site N is forcibly widened and treated.

For example, the balloon catheter 1 can be configured to be a percutaneous transluminal coronary angioplasty (PTCA) dilation balloon catheter used for widening the stenosed site N in a coronary artery. However, for example, the balloon catheter 1 can also be configured to be a balloon catheter used for the purpose of treatment and amelioration of the stenosed site N formed inside a biological organ such as other blood vessels, the bile duct, the trachea, the esophagus, other alimentary canals, the urethra, an aurinasal lumen, and other internal organs.

In this specification, a side of the balloon catheter 1 which is inserted into the biological lumen V (side on which the balloon 20 is disposed) is referred to as a distal side. A side which is positioned on a side opposite to the distal side and on which a manual operation is performed (side on which a hub 30 is disposed) is referred to as a proximal side. A direction, in which the balloon 20 is stretched, is referred to as an axial direction of the balloon. In addition, in description of the embodiments, a distal portion denotes a certain range including a distal end (outermost distal end) and the periphery thereof. A proximal portion denotes a certain range including a proximal end (innermost proximal end) and the periphery thereof. In addition, in this specification, a "circumferential direction" denotes a circumferential direction of the balloon 20.

Figure 1A:
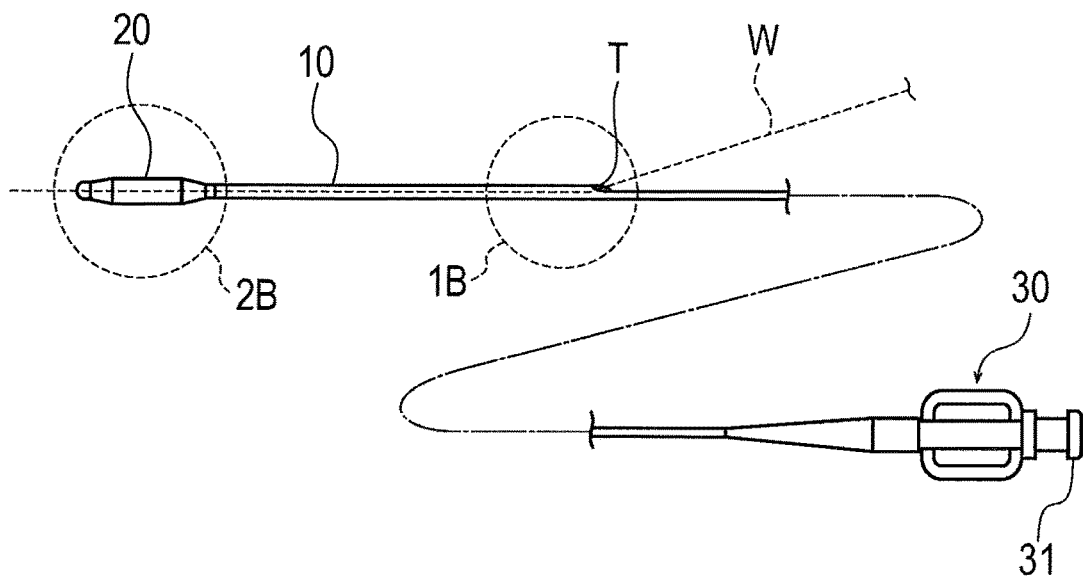
FIG. 1A is a view illustrating a balloon catheter according to Embodiment 1 of the present disclosure.
Figure 2A:
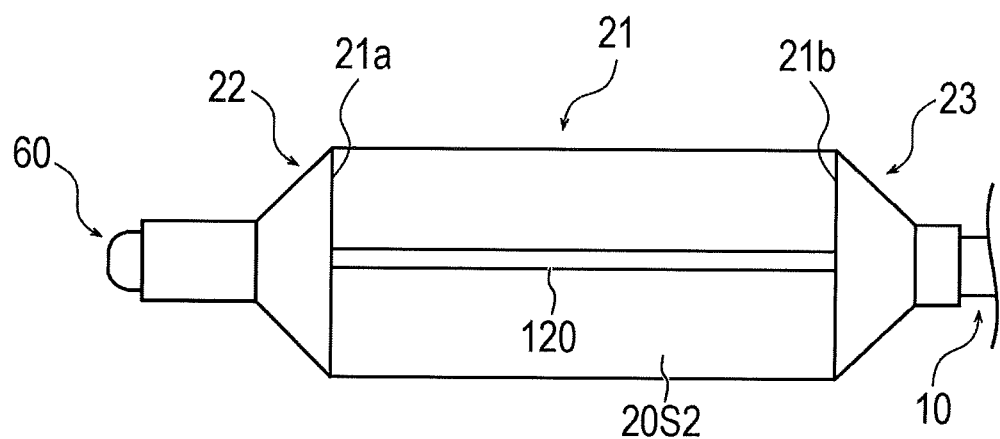
FIG. 2A is a plan view of a balloon of the balloon catheter according to Embodiment 1.
Figure 2B:
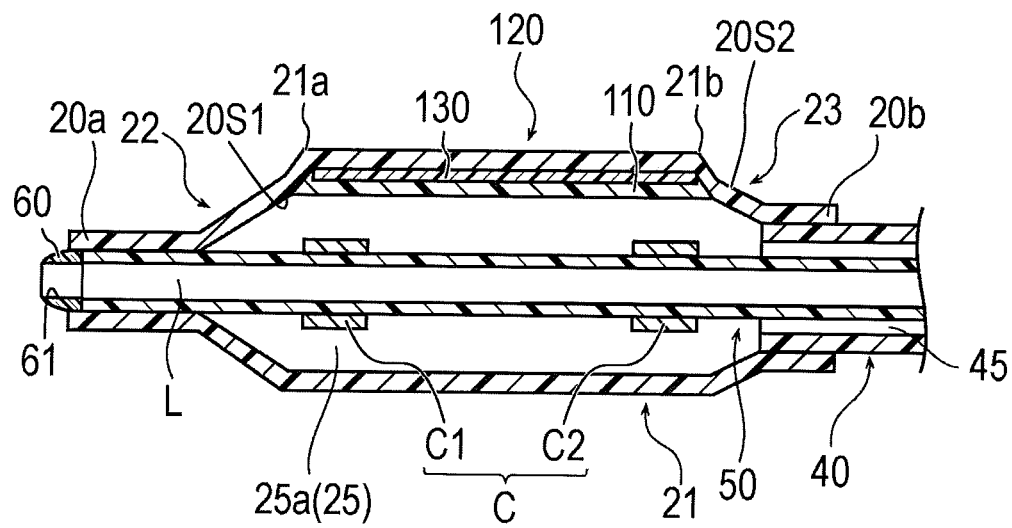
FIG. 2B is an enlarged sectional view of a part indicated with a dotted line area 2B in FIG. 1A.
Figure 3A:
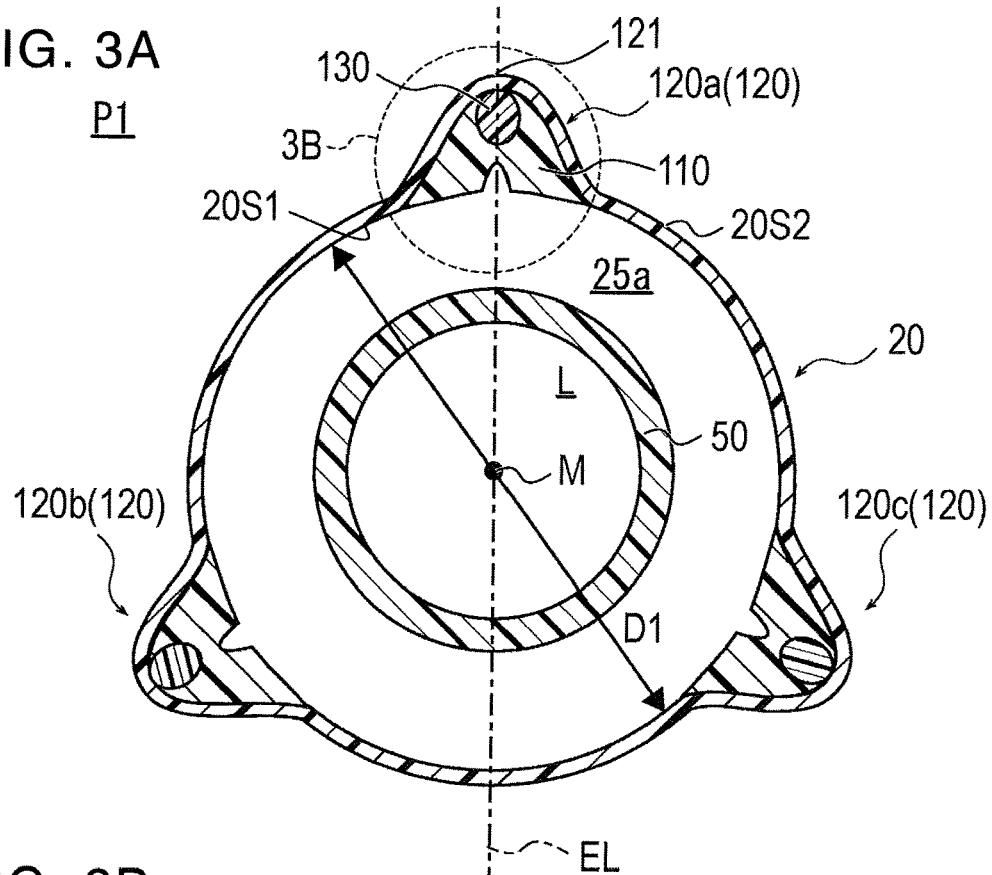
FIG. 3A is a cross-sectional view of the balloon according to Embodiment 1 in a dilated state under a first internal pressure.

In general description with reference to FIGS. 1A, 2B, and 3A, the balloon catheter 1 according to Embodiment 1 has the shaft 10, the balloon 20 (corresponding to dilation member) that is fixed to the shaft 10 on the distal side, an elastic member 110 that is disposed on an inner surface 20S1 of the balloon 20, and the hub 30. The balloon 20 includes projection portions 120 each of which is a part of the balloon 20 protruding in a radial direction due to the elastic member 110 disposed at a position where the inner surfaces 20S1 of the balloon 20 face each other. A material of the elastic member 110 is configured to be a material, which is further stretched than a material of the balloon 20 in the circumferential direction when the balloon 20 dilates. Hereinafter, a configuration of each portion will be described in detail.

Figure 1B:
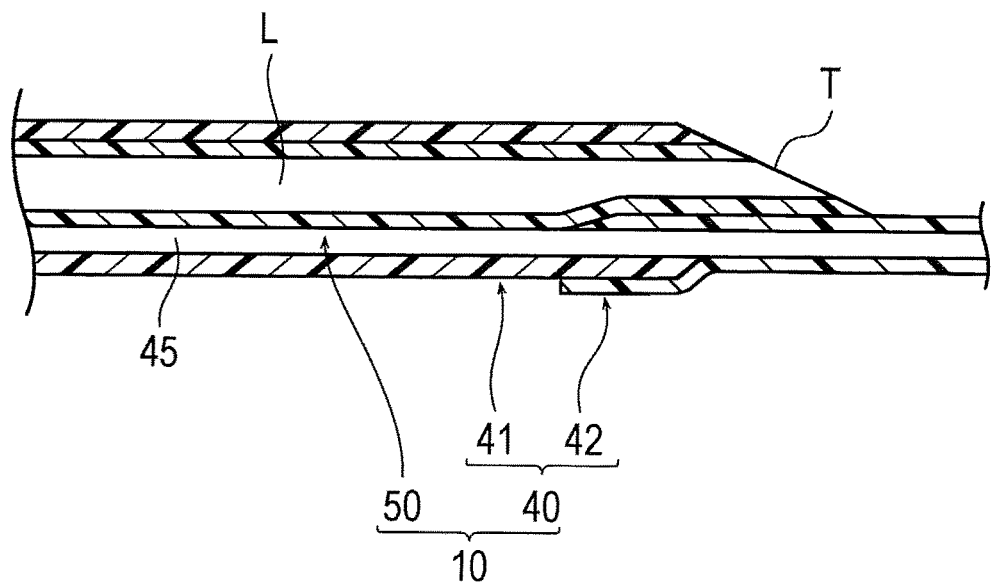
FIG. 1B is an enlarged sectional view of a part indicated with a dotted line area 1B in FIG. 1A.

With reference to FIG. 1B, the shaft 10 has an outer shaft 40, an inner shaft 50, and a guide wire port T.

The outer shaft 40 has a distal side shaft 41 and a proximal side shaft 42 which is connected to the distal side shaft 41 on the proximal side.

The distal side shaft 41 and the proximal side shaft 42 are integrally connected (welded) to the inner shaft 50 in the vicinity of the guide wire port T of the shaft 10.

A lumen (not illustrated) of the distal side shaft 41 and a lumen (not illustrated) of the proximal side shaft 42 form a lumen 45 of the outer shaft 40, which communicates with a lumen 25 of the balloon 20 (refer to FIG. 2B) in a state where the distal side shaft 41 and the proximal side shaft 42 are connected to each other.

As a constituent material of the outer shaft 40, for example, it is possible to use polyolefin such as polyethylene, polypropylene, an ethylene-propylene copolymer, and an ethylene-vinyl acetate copolymer; a thermoplastic resin such as soft polyvinyl chloride; various elastomers such as a polyurethane elastomer, a polyamide elastomer, and a polyester elastomer; or crystalline plastic such as polyamide, crystalline polyethylene, and crystalline polypropylene.

The inner shaft 50 is disposed in the lumen 45 of the outer shaft 40. The inner shaft 50 forms a guide wire lumen L through which a guide wire W is inserted. The proximal side of the guide wire lumen L communicates with the guide wire port T.

As a constituent material of the inner shaft 50, for example, a material similar to that of the outer shaft 40 can be used.

The guide wire port T communicates with the guide wire lumen L of the inner shaft 50. The guide wire port T is formed in the proximal portion of the inner shaft 50.

The balloon catheter 1 is configured to be a so-called rapid exchange-type catheter having the guide wire port T which is formed close to the distal portion side of the shaft 10 and through which the guide wire W can enter and exit.

With reference to FIGS. 2A and 2B, the balloon 20 is fixed to the outer shaft 40 and the inner shaft 50 on the distal side. Specifically, the distal portion 20a of the balloon 20 is fixed to the distal portion of the inner shaft 50. A proximal portion 20b of the balloon 20 is fixed to the distal portion of the outer shaft 40.

The balloon 20 dilates in the radial direction of the shaft 10 due to a fluid (pressurizing medium) infused through the lumen 45 of the outer shaft 40 (dilation lumen).

In accordance with an exemplary embodiment, the balloon 20 includes an intermediate region 21 which has a distal end 21a and a proximal end 21b, a distal side inclination portion 22 which inclines from the distal end 21a of the intermediate region 21 toward the shaft 10, and a proximal side inclination portion 23, which inclines from the proximal end 21b of the intermediate region 21 toward the shaft 10. The intermediate region 21 forms a maximum outer diameter portion and comes into contact with a biological lumen wall in a state where the balloon 20 has dilated.

As a constituent material of the balloon 20, for example, it is possible to use polyolefin such as polyethylene, polypropylene, and an ethylene-propylene copolymer; polyester such as polyethylene terephthalate; a thermoplastic resin such as polyvinyl chloride, an ethylene-vinyl acetate copolymer, a cross-linked ethylene-vinyl acetate copolymer, and polyurethane; polyamide; a polyamide elastomer; a polystyrene elastomer; silicone rubber; or latex rubber.

A contrast marker portion C indicating a position of the balloon 20 is provided in the inner shaft 50.

For example, the contrast marker portion C can be formed of a metal such as platinum, gold, silver, iridium, titanium, and tungsten, or an alloy thereof.

In accordance with an exemplary embodiment, the contrast marker portion C is disposed in the inner shaft 50 at a location corresponding to the intermediate region 21. The contrast marker portion C has a distal side marker C1, which is disposed on the distal end 21a side of the intermediate region 21 of the balloon 20, and a proximal side marker C2, which is disposed on the proximal end 21b *side of the intermediate region* 21.

The distal side marker C1 and the proximal side marker C2 are disposed to indicate a border portion between the distal side inclination portion 22 and the intermediate region 21, and a border portion between the intermediate region 21 and the proximal side inclination portion 23 in the axial direction of the shaft 10. Specifically, in the distal side marker C1, an end surface of the distal side marker C1 on the distal side is disposed at the border portion between the distal side inclination portion 22 and the intermediate region 21. In addition, in the proximal side marker C2, an end surface of the proximal side marker C2 on the proximal side is disposed at the border portion between the intermediate region 21 and the proximal side inclination portion 23.

A distal tip 60 is provided in the inner shaft 50 on the distal side. The distal tip 60 has a tapered shape such that an outer diameter of the distal tip 60 is reduced toward the distal side. A through-hole 61 penetrating the distal tip 60 in the axial direction is formed inside the distal tip 60. Therefore, the through-hole 61 forms a part of the guide wire lumen L.

For example, the distal tip 60 can be formed of a flexible resin member. However, the quality of a material of the distal tip 60 is not particularly limited as long as the distal tip 60 can be fixed to the inner shaft 50.

Due to the distal tip 60 provided on the distal side, the inner shaft 50 can preferably prevent occurrence of damage to a biological organ (intravascular wall) when the distal end of the balloon catheter 1 comes into contact with the biological organ.

With reference to FIG. 1A, the hub 30 has a port 31 through which the hub 30 can be liquid-tightly and air-tightly connected to a supply device (not illustrated) such as an indeflator for supplying a fluid (pressurizing medium). For example, the port 31 of the hub 30 can be formed using a known luer taper configured to allow a fluid tube to be connected to and separated from the port 31 of the hub 30.

The shaft 10 is connected to the hub 30 in a state where the lumen 45 of the outer shaft 40 communicates with a flow path inside the hub 30. A fluid (for example, a contrast agent or a saline solution) used for dilating the balloon 20 is supplied to the lumen 45 of the outer shaft 40 via the port 31 of the hub 30.

Next, the balloon 20 and the elastic member 110 will be described in detail.

With reference to FIG. 3A, the balloon 20 includes the projection portions 120 each of which is a part of the balloon 20 protruding in the radial direction due to the elastic member 110 disposed at a position where the inner surfaces 20S1 of the balloon 20 face each other.

The material of the elastic member 110 is configured to be a material, which is further stretched than the material of the balloon 20 in the circumferential direction when the balloon 20 dilates. The material of the elastic member 110 is not particularly limited. For example, it is possible to use various rubber materials such as natural rubber, butyl rubber, isoprene rubber, butadiene rubber, styrene-butadiene rubber, and silicone rubber; various thermoplastic elastomers such as a polyurethane-based thermoplastic elastomer, a polyester-based thermoplastic elastomer, a polyamide-based thermoplastic elastomer, an olefin-based thermoplastic elastomer, and a styrene-based thermoplastic elastomer; a UV-hardened adhesive such as urethane acrylate; or a mixture thereof.

When the balloon 20 dilates under a first internal pressure P1, a first lumen 25a is formed inside the balloon 20, and the projection portions 120 are formed on an outer surface 20S2 of the balloon 20. For example, the first internal pressure P1 is a nominal pressure of the balloon 20.

When the balloon 20 dilates under the first internal pressure P1, a plurality of projection portions 120 are formed in the circumferential direction. The projection portions 120 include a first projection portion 120a, a second projection portion 120b, and a third projection portion 120c which are formed separately at equal intervals in the circumferential direction when the balloon 20 dilates under the first internal pressure P1.

Figure 4A:
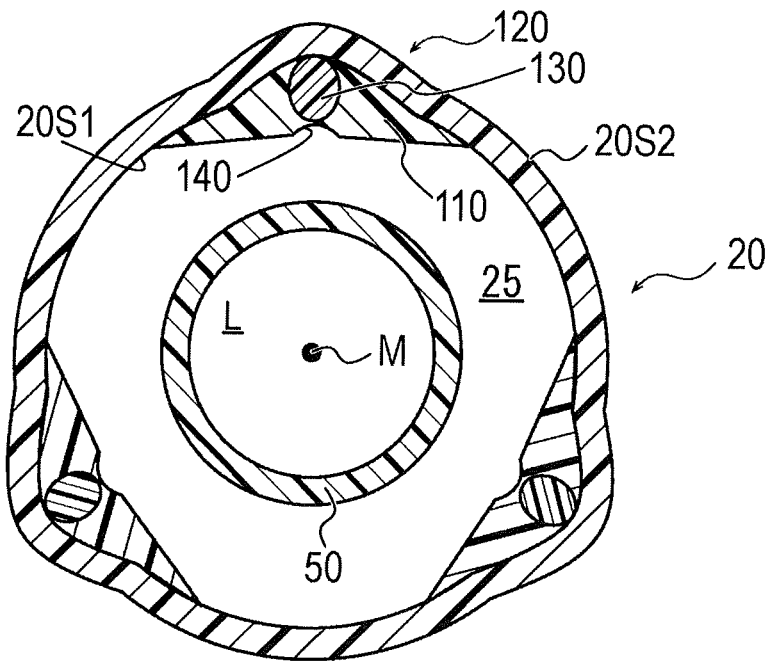
FIG. 4A is a cross-sectional view of the balloon according to Embodiment 1 when the balloon changes from a dilated state under the first internal pressure to a dilated state under a second internal pressure.
Figure 4B:
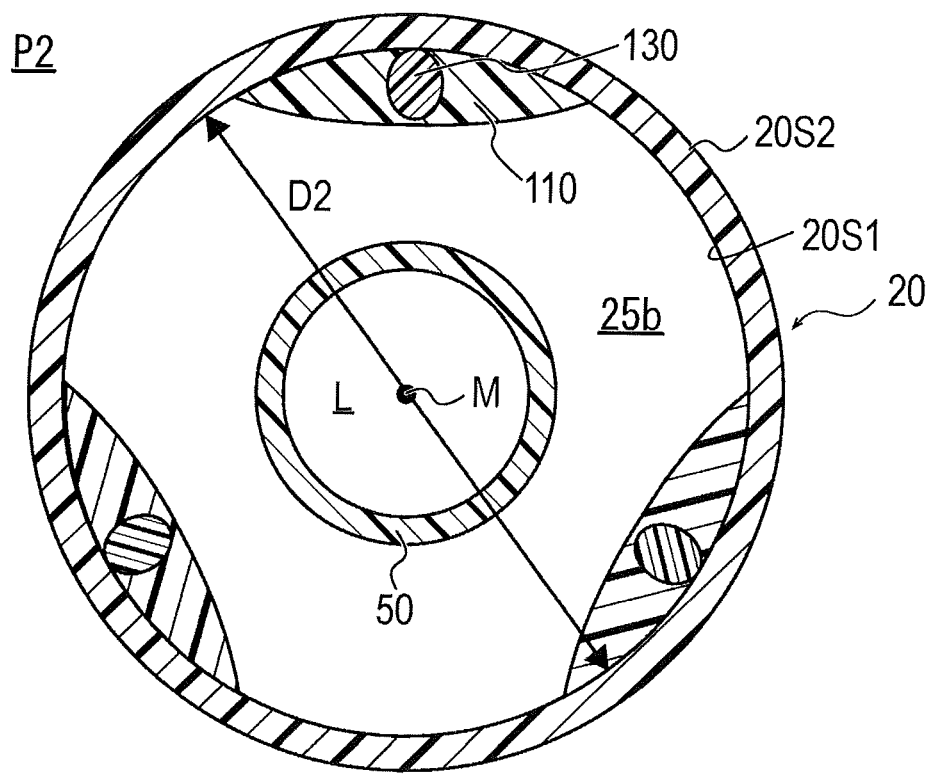
FIG. 4B is a cross-sectional view of the balloon according to Embodiment 1 in a dilated state under the second internal pressure.

With reference to FIGS. 4A and 4B, the projection portions 120 become smaller due to the elastic member 110 stretched in the circumferential direction when the balloon 20 dilates under a second internal pressure P2 higher than the first internal pressure P1. Specifically, as in FIG. 4B, it can be preferable that the projection portions 120 disappear when the balloon 20 dilates under the second internal pressure P2 higher than the first internal pressure P1. When the balloon 20 dilates under the second internal pressure P2, a second lumen 25b greater than the first lumen 25a is formed inside the balloon 20.

The elastic member 110 is stretched in the circumferential direction when the balloon 20 dilates under the second internal pressure P2. When the balloon 20 dilates under the second internal pressure P2, the adhered inner surfaces 20S1 of the balloon 20 are separated from each other due to the elastic member 110.

In accordance with an exemplary embodiment, the second internal pressure P2 is not particularly limited as long as the second internal pressure P2 is higher than the first internal pressure P1. For example, the ratio of the first internal pressure P1 and the second internal pressure P2 can be 1.0:1.2 to 2.0. The size of the second lumen 25b is not limited as long as the second lumen 25b is greater than the first lumen 25a in size. For example, the ratio of an inner diameter D1 of the first lumen 25a and an inner diameter D2 of the second lumen 25b can be 1.00:1.05 to 1.50.

When the balloon 20 is reduced in pressure to a third internal pressure P3 lower than the second internal pressure P2, stretching of the elastic member 110 in the circumferential direction cab be canceled, so that a third lumen 25c smaller than the second lumen 25b is formed and the projection portions 120 are formed again on the outer surface 20S2 of the balloon 20. The shape of the balloon 20 when the balloon 20 is reduced in pressure to the third internal pressure P3 lower than the second internal pressure P2 is substantially the same as the shape of the balloon 20 that has dilated under the first internal pressure P1. The third internal pressure P3 is not particularly limited as long as the third internal pressure P3 is lower than the second internal pressure P2. For example, the third internal pressure P3 can be a nominal pressure as the first internal pressure P1. In accordance with an exemplary embodiment, the inner diameter of the third lumen 25c is substantially equal to the inner diameter D1 of the first lumen 25a in a case where the third internal pressure P3 is the same nominal pressure as the first internal pressure P1.

Figure 3B:
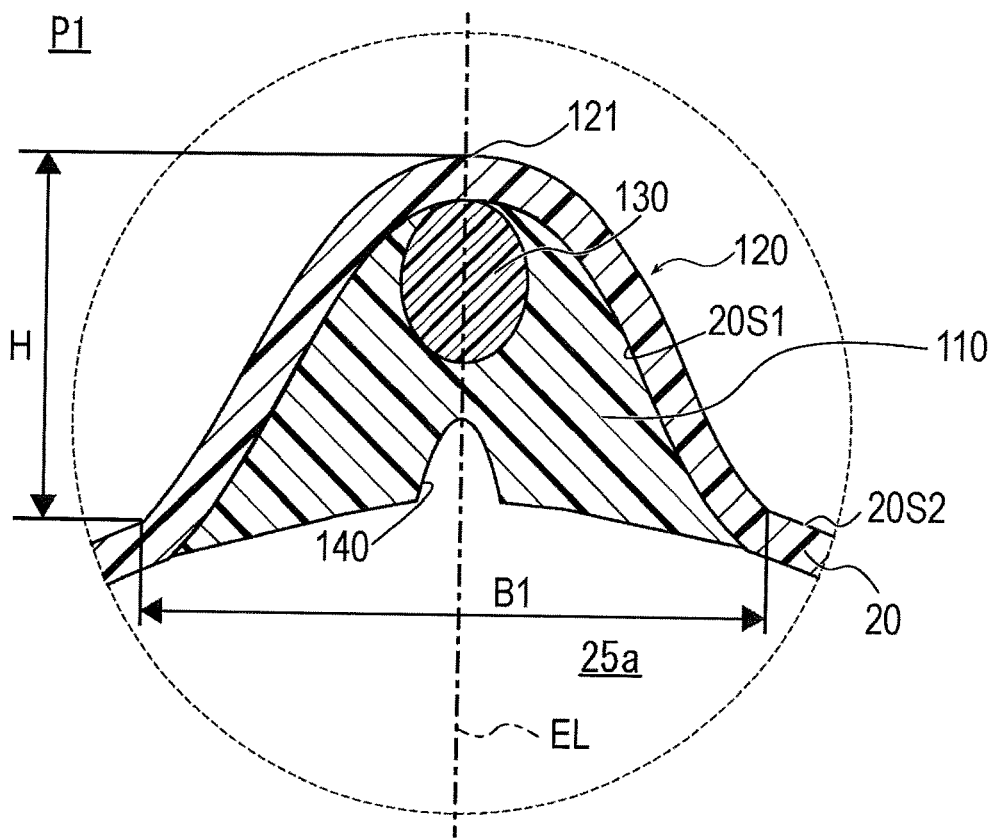
FIG. 3B is an enlarged cross-sectional view of a part indicated with a dotted line area 3B in FIG. 3A.

With reference to FIG. 3B, the projection portion 120 has an apex 121 at which the distance from a center M of the balloon 20 in the radial direction of the inner shaft 50 to the outer surface 20S2 of the balloon 20 becomes the maximum. A protruding amount H of the projection portion 120 formed on the outer surface 20S2 of the balloon 20 when the balloon 20 dilates under the first internal pressure P1 is not particularly limited. For example, the protruding amount H can range approximately from 0.2 mm to 1.0 mm. A width B1 of the projection portion 120 formed on the outer surface 20S2 of the balloon 20 when the balloon 20 dilates under the first internal pressure P1 is not particularly limited. For example, the width B1 can range approximately from 0.2 mm to 1.0 mm.

In accordance with an exemplary embodiment, the elastic member 110 has a rigidity member 130 having rigidity higher than that of the balloon 20 and the elastic member 110 inside the elastic member 110.

A material of the rigidity member 130 is not particularly limited as long as the rigidity member 130 has rigidity higher than those of the balloon 20 and the elastic member 110. For example, it is possible to use metals such as stainless steel, aluminum, an aluminum alloy, titanium, a titanium alloy, copper, a copper-based alloy, tantalum, and a cobalt alloy. In addition, as the material of the rigidity member 130, for example, polyester such as polyvinyl chloride, polyethylene, polypropylene, cyclic polyolefin, polystyrene, poly-(4-methylpentene-1), polycarbonate, an acrylic resin, an acrylonitrile-butadiene-styrene copolymer, polyethylene terephthalate, and polyethylene naphthalate; or a resin such as a butadiene-styrene copolymer and polyamide (for example, nylon 6, nylon 6.6, nylon 6.10, and nylon 12) may be used.

The rigidity member 130 is fixed to the inner surface 20S1 of the balloon 20. In a case where the rigidity member 130 is formed of a metal material, for example, the rigidity member 130 can be fixed to the inner surface 20S1 of the balloon 20 using a known adhesive or the like. In addition, in a case where the rigidity member 130 is formed of a resin material, the rigidity member 130 can be fixed to the inner surface 20S1 of the balloon 20 through heat-welding or the like.

In accordance with an exemplary embodiment, a contour shape of the rigidity member 130 in a cross section perpendicular to the axial direction of the balloon 20 is not particularly limited. For example, the contour shape can be a circular shape or an elliptical shape. In a case where the contour shape of the rigidity member 130 in a cross section perpendicular to the axial direction of the balloon 20 is an elliptical shape, it can be preferable that a major axis of the elliptical shape is disposed on a straight line EL connecting the apex 121 of the projection portion 120 and the center M of the balloon 20.

Note that, the rigidity member 130 does not have to be fixed to the inner surface 20S1 of the balloon 20 as long as rigidity of the projection portion 120 can be enhanced when the balloon 20 dilates under the first internal pressure P1. In addition, a plurality of rigidity members 130 may be present inside the elastic member 110 as long as a force of the projection portion 120 pressed to the stenosed site N is not dispersed and rigidity of the projection portion 120 can be enhanced when the balloon 20 dilates under the first internal pressure P1.

In accordance with an exemplary embodiment, the elastic member 110 has a stretch starting portion 140 which is recessed in the radial direction of the shaft 10 when the balloon 20 dilates under the first internal pressure P1. The stretch starting portion 140 is recessed in the elastic member 110 in the radial direction of the shaft 10 from a surface facing the lumen 25 of the balloon 20. The stretch starting portion 140 is disposed on the straight line EL connecting the apex 121 of the projection portion 120 and the center M of the balloon 20 in a cross section perpendicular to the axial direction of the balloon 20.

With reference to FIGS. 2A and 2B, the projection portions 120 are formed in the intermediate region 21. Specifically, the projection portions 120 are continuously formed from the distal end 21a toward the proximal end 21b of the intermediate region 21 when the balloon 20 dilates under the first internal pressure P1. The rigidity member 130 continuously extends from the distal end 21a toward the proximal end 21b of the intermediate region 21 when the balloon 20 dilates under the first internal pressure P1.

Figure 5A:
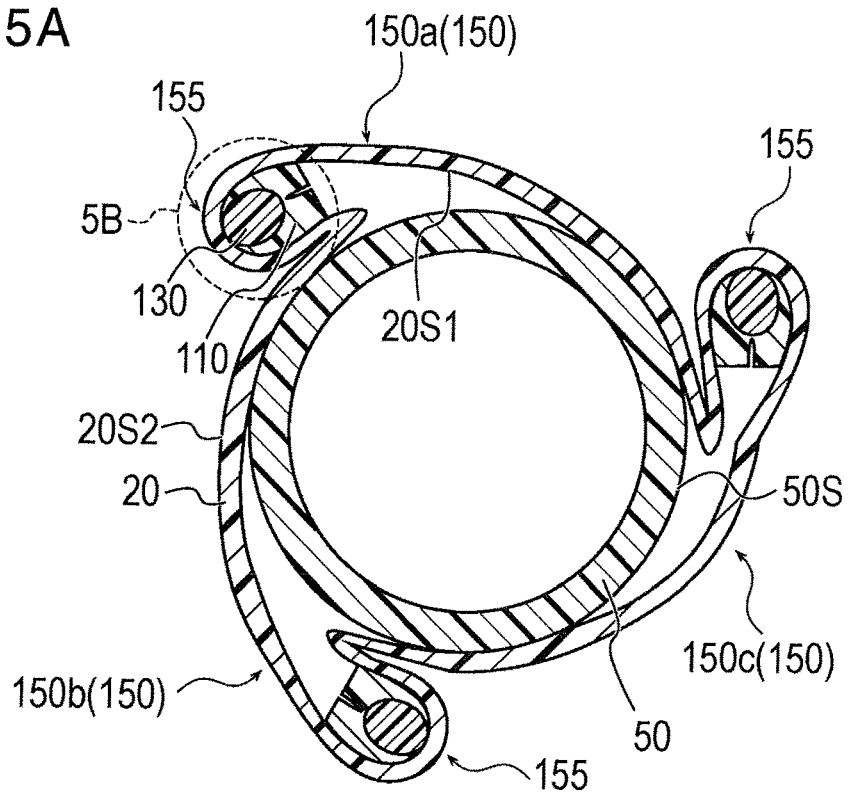
FIG. 5A is a cross-sectional view of the balloon according to Embodiment 1 in a deflated state.

In accordance with an exemplary embodiment, with reference to FIG. 5A, the balloon 20 has vane portions 150 wound around the inner shaft 50 in a deflated state. A deflated state indicates a state where no internal pressure is applied to the lumen 25 of the balloon 20.

Figure 5B:
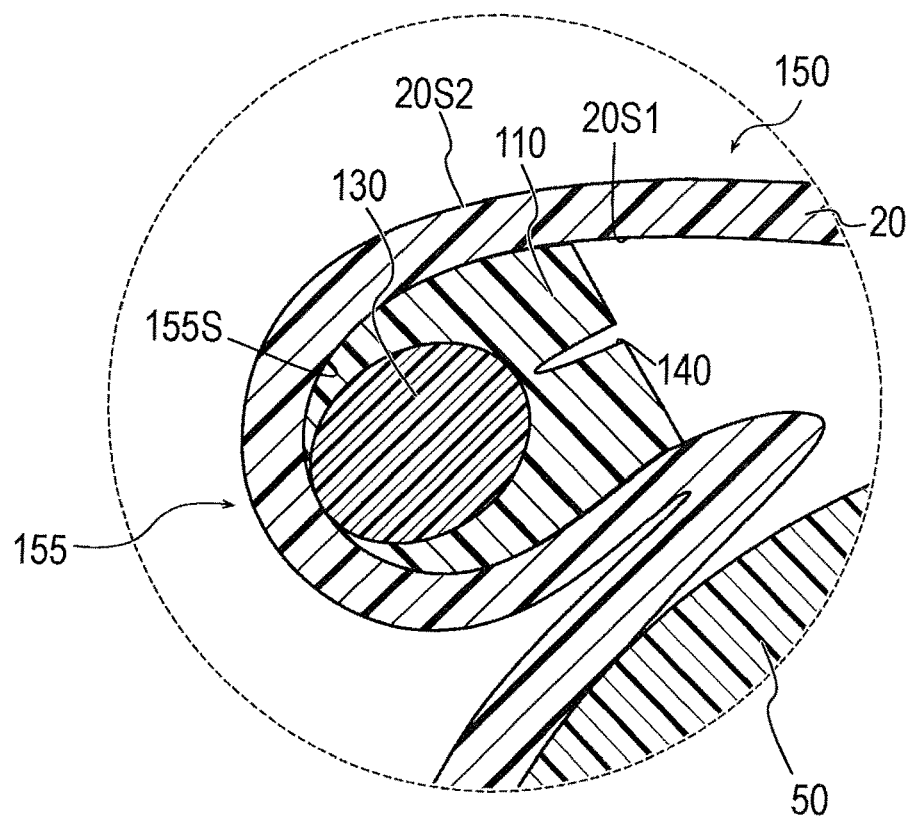
FIG. 5B is an enlarged cross-sectional view of a part indicated with a dotted line area 5B in FIG. 5A.

With reference to FIG. 5B, the vane portion 150 includes an apex portion 155 disposed on an end portion side of the vane portion 150 in a winding direction. The apex portion 155 is bent with respect to the radial direction of the shaft 10 such that the outer surfaces 20S2 of the balloon 20 overlap each other in the radial direction of the shaft 10. The elastic member 110 is disposed on an inner surface 155S of the apex portion 155 of the vane portion 150. The apex portion 155 of the vane portion 150 forms the projection portion 120 when the balloon 20 dilates under the first internal pressure P1 or the third internal pressure P3.

A plurality of vane portions 150 are formed in the circumferential direction in a state where the balloon 20 has deflated. The vane portions 150 include a first vane portion 150a, a second vane portion 150b, and a third vane portion 150c which are formed separately at equal intervals in the circumferential direction in a state where the balloon 20 has deflated.

The first vane portion 150a, the second vane portion 150b, and the third vane portion 150c are curved in the same orientation in the circumferential direction.

Next, a method of using the balloon catheter 1 will be described.

Figure 6:
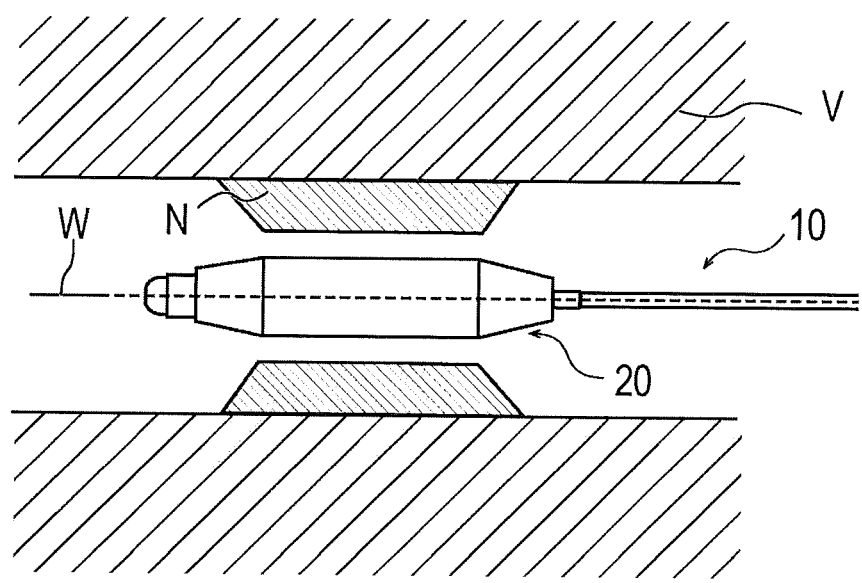
FIG. 6 is a view illustrating a situation in which the balloon according to Embodiment 1 is disposed in a stenosed site.

First, a practitioner inserts the guide wire W through the biological lumen V, which causes the distal side of the guide wire W to pass through the stenosed site N (lesion area), and inserts the balloon catheter 1 into the biological lumen V along the guide wire W. With reference to FIG. 6, the practitioner delivers the balloon catheter 1 inserted into the biological lumen V to the stenosed site N and disposes the balloon 20 in the stenosed site N of the biological lumen V. When the balloon catheter 1 is delivered to and is disposed in the stenosed site N, as illustrated in FIGS. 5A and 5B, the balloon 20 is in a deflated state.

Figure 7A:
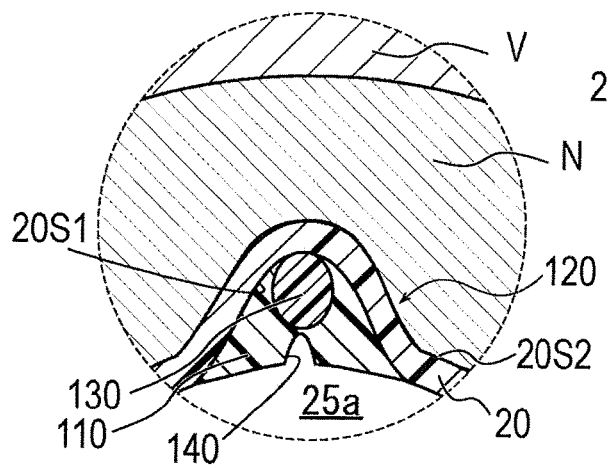
FIG. 7A is a cross-sectional view illustrating a situation in which the balloon according to Embodiment 1 disposed in a stenosed site dilates under the first internal pressure.

Next, with reference to FIG. 7A, the practitioner infuses a fluid into the lumen 25 of the balloon 20 in a state where the balloon 20 is disposed in the stenosed site N, so that the balloon 20 dilates under the first internal pressure P1 and the projection portions 120 are formed on the outer surface 20S2 of the balloon 20. The fluid can be infused into the lumen 25 of the balloon 20 via the port 31 of the hub 30 and the lumen 45 of the outer shaft 40. In accordance with an exemplary embodiment, a nick can be made in the stenosed site N due to the projection portions 120 formed on the outer surface 20S2 of the balloon 20.

Figure 7C:
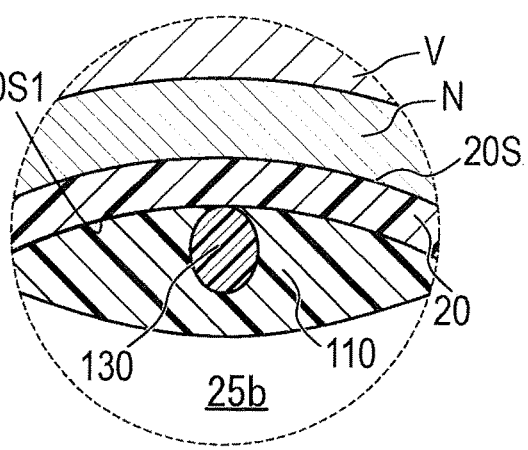
FIG. 7C is a cross-sectional view illustrating a situation in which the balloon according to Embodiment 1 disposed in a stenosed site dilates under the second internal pressure.
Figure 7B:
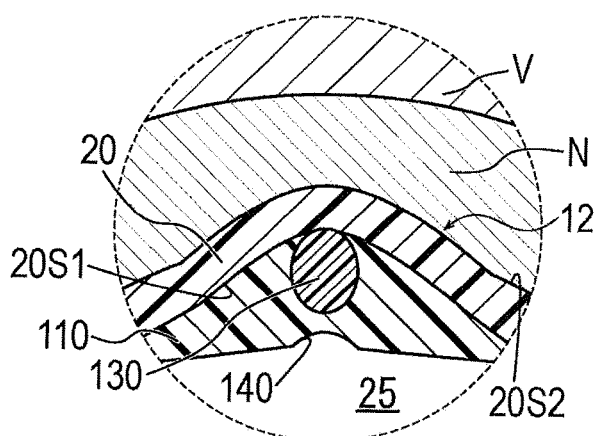
FIG. 7B is a cross-sectional view illustrating a situation in which the balloon according to Embodiment 1 disposed in a stenosed site changes from a dilated state under the first internal pressure to a dilated state under the second internal pressure.

Next, with reference to FIGS. 7B and 7C, the practitioner infuses the fluid into the lumen 25 of the balloon 20 that has dilated under the first internal pressure P1, so that the balloon 20 dilates under a pressure shifted from the first internal pressure P1 to the second internal pressure P2, and the projection portions 120 become small or disappear from the outer surface 20S2 of the balloon 20. In accordance with an exemplary embodiment, the practitioner can further widen the stenosed site N in which a nick is made, due to the balloon 20 that has dilated under the second internal pressure P2. In this case, the projection portions 120 on the outer surface 20S2 of the balloon 20 become small or the projection portions 120 disappear from the outer surface 20S2 of the balloon 20, so that the balloon 20 can evenly apply the dilation pressure to the stenosed site N along the circumferential direction.

Figure 7D:
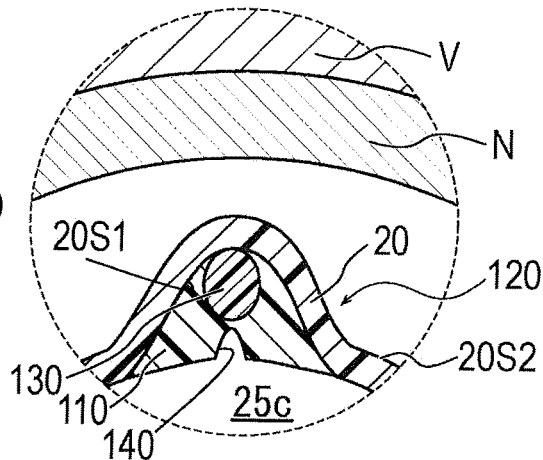
FIG. 7D is a cross-sectional view illustrating a situation in which the balloon according to Embodiment 1 disposed in a stenosed site dilates under a third internal pressure.

Next, with reference to FIG. 7D, the practitioner discharges the fluid from the lumen 25 of the balloon 20 which has dilated under the second internal pressure P2, so that the internal pressure of the balloon 20 is reduced from the second internal pressure P2 to the third internal pressure P3. In accordance with an exemplary embodiment, the fluid can be discharged from the lumen 25 of the balloon 20 via the lumen 45 of the outer shaft 40 and the port 31 of the hub 30.

Next, the practitioner further discharges the fluid from the lumen 25 of the balloon 20 which has been reduced in pressure from the second internal pressure P2 to the third internal pressure P3, so that the balloon 20 deflates. In accordance with an exemplary embodiment, the practitioner removes the deflated balloon 20 out of the body via the biological lumen V.

Note that, the practitioner may cause the balloon 20 to deflate by discharging all the fluid of the lumen 25 of the balloon 20 when the internal pressure of the balloon 20 is reduced from the second internal pressure P2 to the third internal pressure P3 by discharging the fluid from the lumen 25 of the balloon 20 which has dilated under the second internal pressure P2. In such a case, the practitioner can easily remove the deflated balloon 20 out of the body via the biological lumen V.

In the balloon catheter 1 according to the present embodiment, when the balloon 20 dilates under the first internal pressure P1, the projection portions 120 are formed on the outer surface 20S2 of the balloon 20. Accordingly, the balloon catheter 1 can make a nick in the stenosed site N due to the balloon 20, which has dilated under the first internal pressure P1. In the balloon catheter 1, when the balloon 20 dilates under a pressure shifted from the first internal pressure P1 to the second internal pressure P2, the projection portions 120 on the outer surface 20S2 of the balloon 20 become small (the projection portions 120 on the outer surface 20S2 of the balloon 20 disappear), and the outer diameter of the balloon 20 increases. Accordingly, the balloon catheter 1 can make a nick in the stenosed site N using one balloon catheter and can cause the dilation pressure of the balloon 20 to evenly act on the stenosed site N in which the nick is made. Therefore, the balloon catheter 1 can make a nick in the stenosed site N and can preferably widen the stenosed site N in which the nick is made.

In addition, in the balloon catheter 1 according to the present embodiment, the elastic member 110 is disposed on the inner surface 20S1 of the balloon 20. The elastic member 110 is stretched when the balloon 20 dilates under the second internal pressure P2 higher than the first internal pressure P1. Accordingly, in the balloon catheter 1, when the balloon 20 dilates under the second internal pressure P2, rigidity of the balloon 20 increases due to the elastic member 110 disposed on the inner surface 20S1 of the balloon 20, even if the projection portions 120 on the outer surface 20S2 of the balloon 20 are in a small state or in a disappeared state. Therefore, in the balloon catheter 1, when the balloon 20 dilates under the second internal pressure P2, the dilation pressure of the balloon 20 can be more reliably applied to the stenosed site N in which a nick is made. Therefore, the balloon catheter 1 can make a nick in the stenosed site N and can more preferably widen the stenosed site N in which the nick is made.

In accordance with an exemplary embodiment, in the balloon catheter 1 according to the present embodiment, the elastic member 110 has the rigidity member 130 having rigidity higher than that of the balloon 20 and the elastic member 110 inside the elastic member 110. Accordingly, rigidity of the projection portions 120 can be improved. Therefore, the balloon catheter 1 can more reliably make a nick in the stenosed site N when the balloon 20 dilates under the first internal pressure P1.

In addition, in the balloon catheter 1 according to the present embodiment, the rigidity member 130 can be fixed to the inner surface 20S1 of the balloon 20. Accordingly, in the balloon catheter 1, when the balloon 20 dilates under the first internal pressure P1, the rigidity member 130 does not move, and it is possible to more reliably improve rigidity of the projection portions 120 at locations, which are in contact with the stenosed site N. Therefore, the balloon catheter 1 can more reliably make a nick with respect to the stenosed site N when the balloon 20 dilates under the first internal pressure P1, while forces transmitted to the stenosed site N by the projection portions 120 are not dispersed.

In addition, in the balloon catheter 1 according to the present embodiment, the projection portions 120 are formed in the intermediate region 21. The intermediate region 21 is a region, which comes into contact with the stenosed site N when the balloon 20 dilates. Therefore, the balloon catheter 1 can more reliably make a nick with respect to the stenosed site N when the balloon 20 dilates under the first internal pressure P1, due to the projection portions 120 formed in the intermediate region 21.

In addition, in the balloon catheter 1 according to the present embodiment, the projection portions 120 can be continuously formed from the distal end 21a toward the proximal end 21b of the intermediate region 21 when the balloon 20 dilates under the first internal pressure P1. Accordingly, the balloon catheter 1 can continuously make nicks from the distal end 21a toward the proximal end 21b of the intermediate region 21 with respect to the stenosed site N when the balloon 20 dilates under the first internal pressure P1. Therefore, the balloon catheter 1 can more reliably widen the stenosed site N when the balloon 20 dilates under a pressure shifted from the first internal pressure P1 to the second internal pressure P2.

In accordance with an exemplary embodiment, in the balloon catheter 1 according to the present embodiment, the elastic member 110 has the stretch starting portion 140 which is recessed in the radial direction of the shaft 10 when the balloon 20 dilates under the first internal pressure P1. Accordingly, when the balloon 20 dilates under a pressure shifted from the first internal pressure P1 to the second internal pressure P2, the elastic member 110 can be smoothly stretched while having the stretch starting portion 140 as a starting point. Therefore, the adhered inner surfaces 20S1 of the balloon 20 can be smoothly separated from each other due to the elastic member 110. Therefore, in the balloon catheter 1, when the balloon 20 dilates under a pressure shifted from the first internal pressure P1 to the second internal pressure P2, the projection portions 120 can become small or disappear smoothly. Therefore, it is possible to cause a dilation pressure of the balloon 20 to reliably and evenly act on the stenosed site N in which a nick is made.

In accordance with an exemplary embodiment, in the balloon catheter 1 according to the present embodiment, the balloon 20 can have a plurality of vane portions 150a, 150b, and 150c wound around the inner shaft 50 in a deflated state in which no internal pressure is applied to the inside of the balloon 20. Accordingly, in the balloon catheter 1, the outer diameter of the balloon 20 in a deflated state can become smaller due to the vane portions 150 wound around the inner shaft 50. Therefore, in the balloon catheter 1, passing characteristics of the balloon 20 in the biological lumen V can be improved.

Figure 8A:
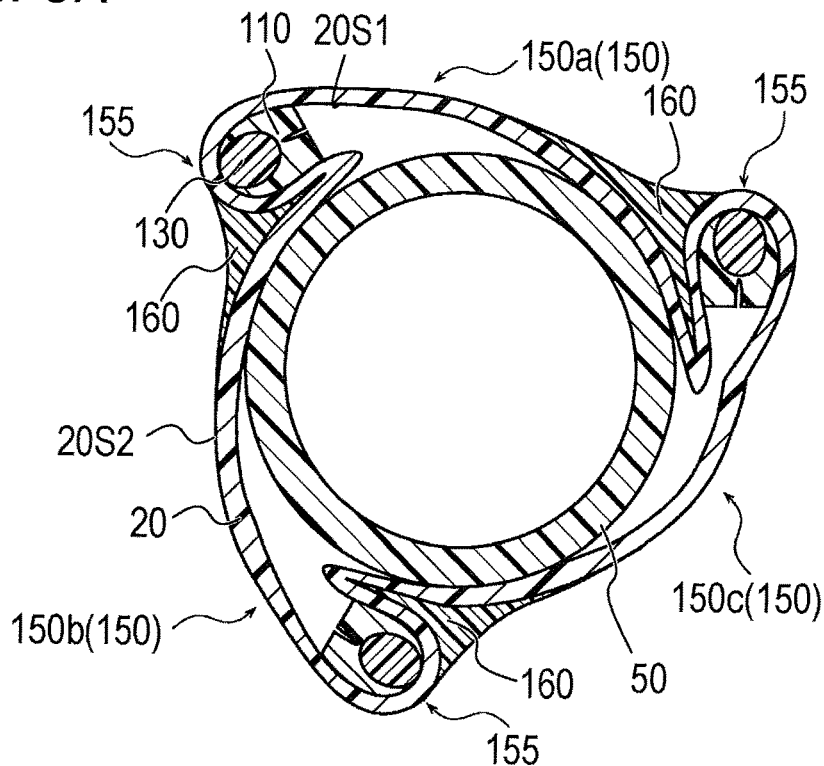
FIG. 8A is a cross-sectional view of a balloon of a balloon catheter according to the modification example of Embodiment 1 in a deflated state.

With reference to FIG. 8A, the balloon 20 may have elastic outer surface portions 160 disposed on the outer surface 20S2 of the balloon 20. A material of the elastic outer surface portion 160 can be configured to be a material, which is further stretched than the material of the balloon 20 in the circumferential direction when the balloon 20 dilates. In accordance with an exemplary embodiment, the elastic outer surface portions 160 are disposed between the first vane portion 150a and the second vane portion 150b, between the second vane portion 150b and the third vane portion 150c, and the third vane portion 150c and the first vane portion 150a in a deflated state in which no internal pressure is applied to the inside of the balloon 20.

Figure 8B:
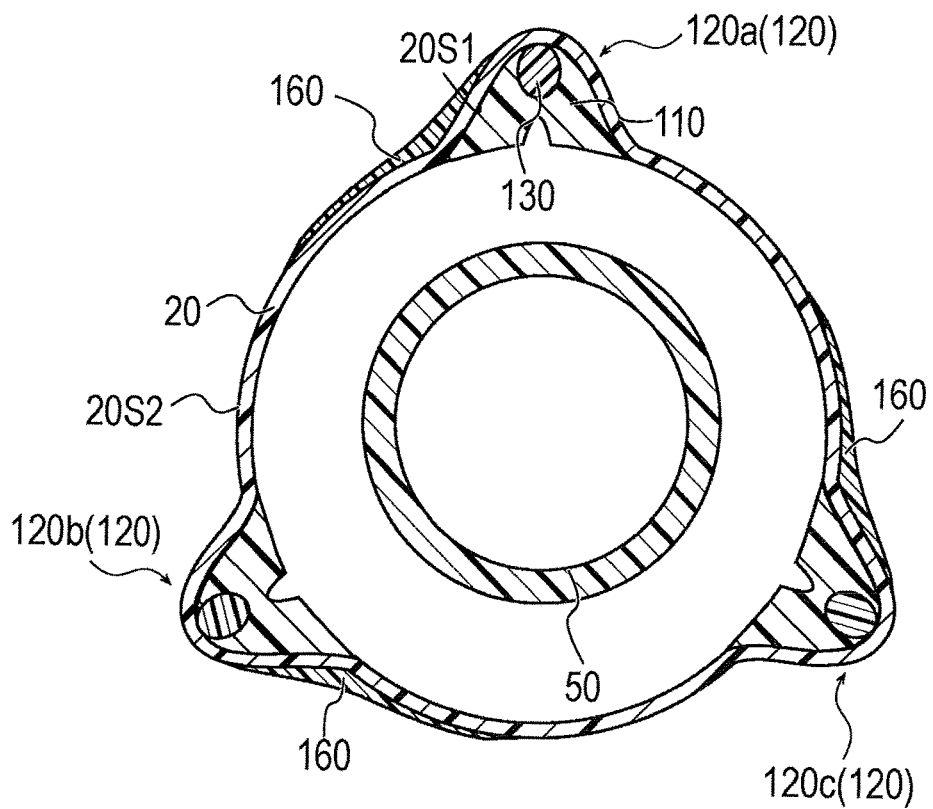
FIG. 8B is a cross-sectional view of the balloon of the balloon catheter according to the modification example of Embodiment 1 in a dilated state under the first internal pressure.

With reference to, FIG. 8B the elastic outer surface portions 160 are stretched in the circumferential direction when the balloon 20 dilates. When the elastic outer surface portion 160 is stretched in the circumferential direction, a restoring force is generated inside thereof. Therefore, the elastic outer surface portion 160 generates a force that tends to cause the balloon 20 to return to the original shape when the dilated balloon 20 deflates.

The material forming the elastic outer surface portion 160 is not particularly limited as long as the material is a material which is further stretched than the material of the balloon 20 in the circumferential direction when the balloon 20 dilates. A material similar to the above-described material can be used as the material of the elastic member 110.

In a balloon catheter according to the present modification example, a restoring force is generated inside the elastic outer surface portion 160 due to the elastic outer surface portion 160 stretched in the circumferential direction when the balloon 20 dilates. Accordingly, in the balloon catheter according to the present modification example, the vane portions 150 can be reliably wound around the inner shaft 50 due to a restoring force of the elastic outer surface portion 160 disposed between the vane portions 150 adjacent to each other when the balloon 20 changes from a dilated state to a deflated state. Therefore, in the balloon catheter according to the present modification example, when the balloon 20 deflates again from a dilated state, the balloon 20 is likely to automatically return to the outer diameter before dilation, and the outer diameter of the balloon 20 can be maintained in a small state before dilation.

In the above-described Embodiment 1, in accordance with an exemplary embodiment, the inside of the projection portion 120 can be filled with the elastic member 110. However, the projection portion may have a space portion between the inner surface 20S1 of the balloon 20 and the elastic member 110. Hereinafter, a balloon catheter according to Embodiment 2 will be described. In the description below, the same reference signs as those of the above-described Embodiment 1 are applied to the same members as those of the above-described Embodiment 1, and description will be omitted.

Figure 9A:
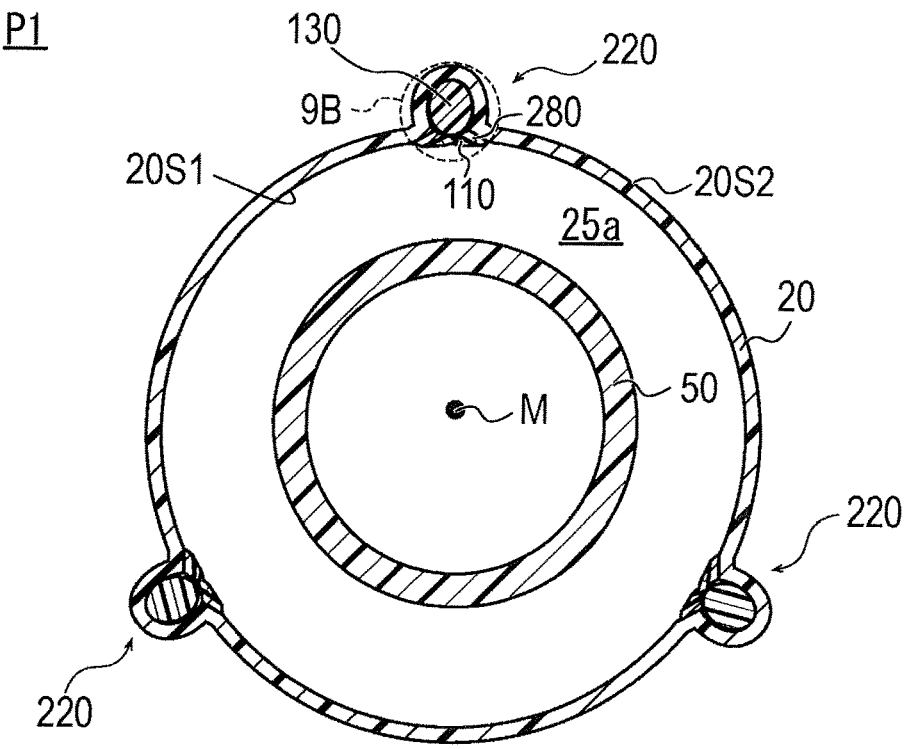
FIG. 9A is a cross-sectional view of a balloon of a balloon catheter according to Embodiment 2 in a dilated state under the first internal pressure.
Figure 9B:
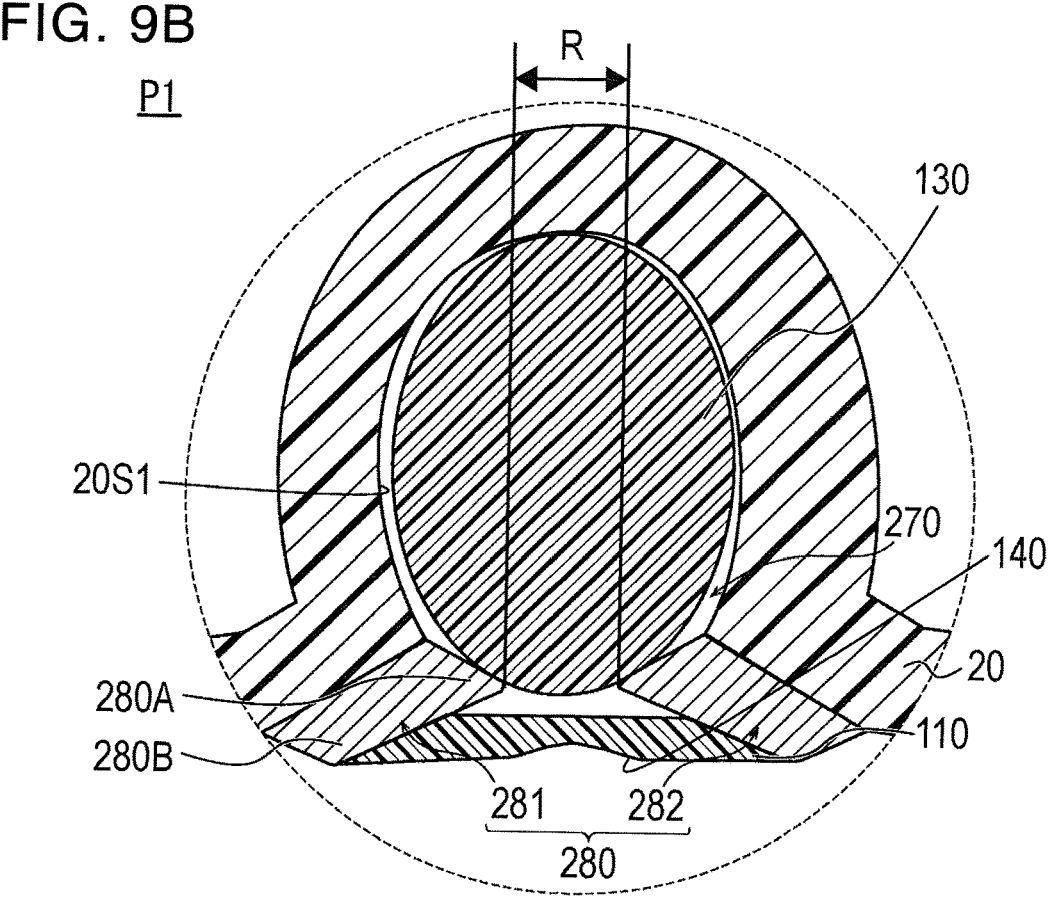
FIG. 9B is an enlarged cross-sectional view of a part indicated with a dotted line area 9B in FIG. 9A.

With reference to FIGS. 9A and 9B, in the balloon catheter according to Embodiment 2, each of projection portions 220 has a space portion 270 between the inner surface 20S1 of the balloon 20 and the elastic member 110. The rigidity member 130 is disposed in the space portion 270. Note that, the "space portion" indicates a clearance formed between the inner surface 20S1 of the balloon 20 and the elastic member 110. That is, a member stuffing the inside of the projection portion 220 (elastic member 110 or the like filling the inside of the projection portion 120 in the embodiment described above) is not disposed inside the projection portion 220 other than the rigidity member 130 in a state where the balloon 20 has deflated.

The size of the space portion 270 is minimized in a state where the balloon 20 has deflated. The size of the space portion 270 in a state where the balloon 20 has deflated is not particularly limited as long as the rigidity member 130 can be disposed. The size of the space portion 270 in a state where the balloon 20 has deflated may be substantially equal to the size of the rigidity member 130 or may be greater than the size of the rigidity member 130.

The rigidity member 130 is fixed to the inner surface 20S1 of the balloon 20. The method of fixing the rigidity member 130 to the inner surface 20S1 of the balloon 20 is not particularly limited. The rigidity member 130 may be fixed by a method similar to the above-described method in the above-described Embodiment 1. Note that, similar to the above-described Embodiment 1, the rigidity member 130 does not have to be fixed to the inner surface 20S1 of the balloon 20 as long as rigidity of the projection portions 120 can be enhanced when the balloon 20 dilates under the first internal pressure P1.

The balloon 20 has a support member 280, which supports the rigidity member 130 inside the balloon 20 when balloon 20 dilates under the first internal pressure P1. The support member 280 is disposed between the rigidity member 130 and the elastic member 110. Accordingly, the support member 280 can help prevent the rigidity member 130 from moving in a direction to the inside of the balloon 20, can enhance rigidity of the projection portions 220, and can increase a force transmitted to the stenosed site N by the projection portions 220 when the balloon 20 dilates under the first internal pressure P1 and the projection portions 220 pressurize the stenosed site N.

In addition, the support member 280 can be fixed to the inner surface 20S1 of the balloon 20. The elastic member 110 is fixed to the support member 280. Accordingly, the elastic member 110 causes the inner surfaces 20S1 of the balloon 20 to adhere to each other via the support member 280. Therefore, the support member 280 can preferably support the rigidity member 130 when the balloon 20 dilates under the first internal pressure P1.

A material of the support member 280 is not particularly limited. For example, a material similar to the above-described material can be used as the material of the rigidity member 130.

The support member 280 has a first region 280A which supports the rigidity member 130 when the balloon 20 dilates under the first internal pressure P1, and a second region 280B which is formed on the center M side of the balloon 20 closer than the first region 280A. The elastic member 110 is disposed in the second region 280B.

Similar to the above-described Embodiment 1, when the balloon 20 dilates under the first internal pressure P1, the first lumen 25a is formed inside the balloon 20, and the projection portions 220 are formed on the outer surface 20S2 of the balloon 20. The first region 280A of the support member 280 comes into contact with the rigidity member 130 when the balloon 20 dilates under the first internal pressure P1.

Figure 10A:
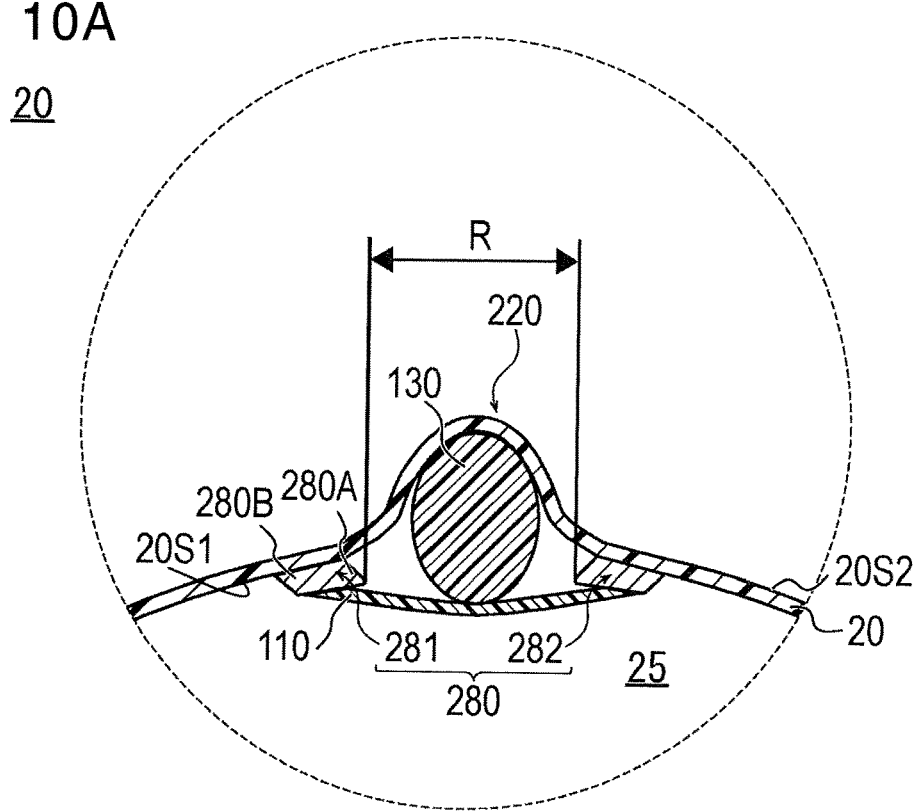
FIG. 10A is an enlarged cross-sectional view in the vicinity of a projection portion of the balloon according to Embodiment 2 when the balloon change from a dilated state under the first internal pressure to a dilated state under the second internal pressure.
Figure 10B:
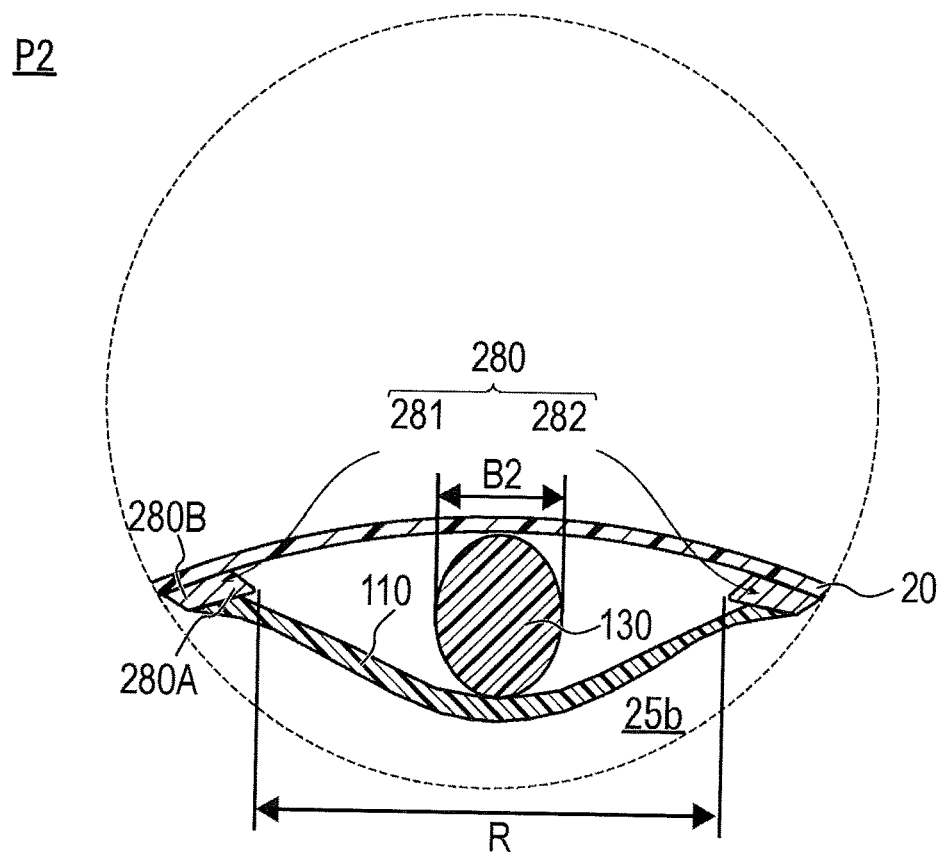
FIG. 10B is an enlarged cross-sectional view of the balloon according to Embodiment 2 in a dilated state under the second internal pressure.

Similar to the above-described Embodiment 1, as illustrated in FIGS. 10A and 10B, the projection portions 220 become small when the balloon 20 dilates under the second internal pressure P2 higher than the first internal pressure P1. Specifically, as illustrated in FIG. 10b, it is preferable that the projection portions 220 disappear when the balloon 20 dilates under the second internal pressure P2 higher than the first internal pressure P1. When the balloon 20 dilates under the second internal pressure P2, the second lumen 25b, which is larger than the first lumen 25a, is formed inside the balloon 20.

The elastic member 110 is stretched in the circumferential direction when the balloon 20 dilates under the second internal pressure P2. When the balloon 20 dilates under the second internal pressure P2, the adhered inner surfaces 20S1 of the balloon 20 are separated from each other due to the elastic member 110.

When the balloon 20 dilates under a pressure shifted from the first internal pressure P1 to the second internal pressure P2, the contact state between the first region 280A of the support member 280 and the rigidity member 130 is canceled.

The support member 280 has a first support member 281 and a second support member 282 which are separated from each other when the balloon 20 dilates under the second internal pressure P2. A distance R between the first support member 281 and the second support member 282 increases in accordance with an increase of the internal pressure of the balloon 20. The distance R between the first support member 281 and the second support member 282 (distance between the first support member 281 and the second support member 282 in the circumferential direction) in a state where the balloon 20 dilates under the second internal pressure P2 is greater than a width B2 of the rigidity member 130 (length of the rigidity member 130 in the circumferential direction) in a cross section perpendicular to the axial direction of the balloon 20 and in a state where the balloon 20 dilates under the first internal pressure P1.

Similar to the above-described Embodiment 1, when the balloon 20 is reduced in pressure to the third internal pressure P3, which is lower than the second internal pressure P2, stretching of the elastic member 110 in the circumferential direction is canceled, so that the third lumen 25c, which is smaller than the second lumen 25b is formed and the projection portions 220 are formed again on the outer surface 20S2 of the balloon 20. The shape of the balloon 20 when the pressure is reduced in pressure to the third internal pressure P3 lower than the second internal pressure P2 is substantially equal to the shape of the balloon 20 that has dilated under the first internal pressure P1.

Figure 11A:
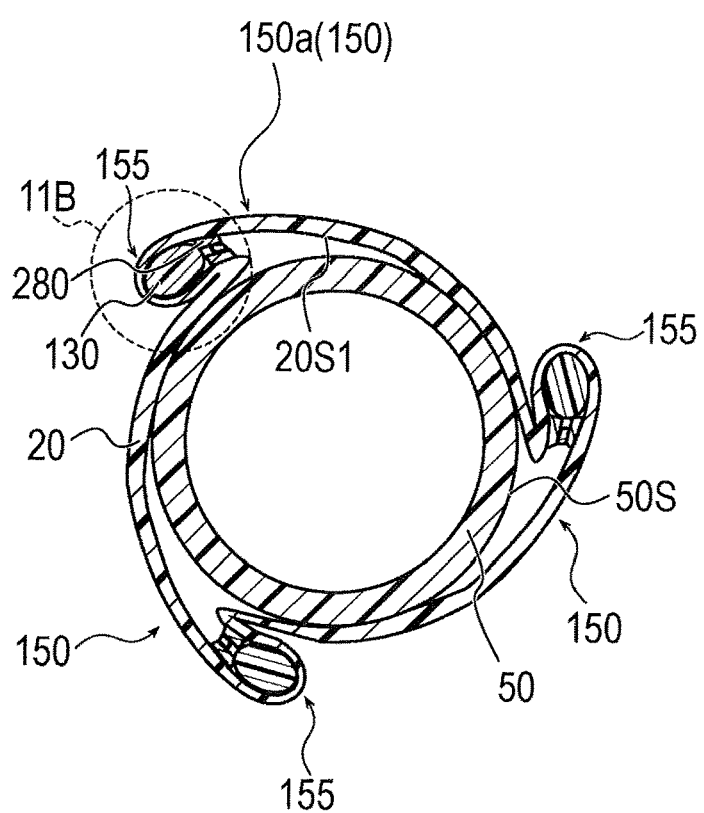
FIG. 11A is a cross-sectional view of the balloon according to Embodiment 2 in a deflated state.
Figure 11B:
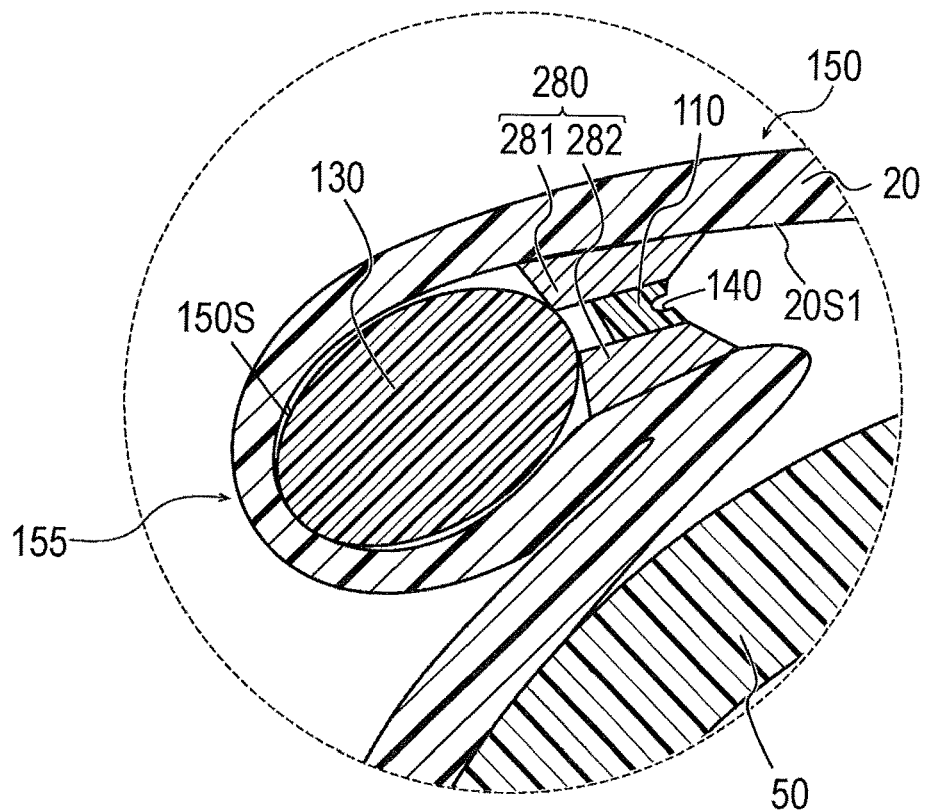
FIG. 11B is an enlarged cross-sectional view of a part indicated with a dotted line area 11B in FIG. 11A.

Similar to the above-described Embodiment 1, with reference to FIGS. 11A and 11B, the balloon 20 can have vane portions 150 wound around the shaft 10 in a deflated state. The vane portion 150 includes the apex portion 155 disposed on the end portion side of the vane portion 150 in the winding direction. The apex portion 155 can be bent with respect to the radial direction of the shaft 10 such that the outer surface 20S2 of the balloon 20 overlap each other in the radial direction of the shaft 10. The elastic member 110 is disposed on the inner surface 155S of the apex portion 155 of the vane portion 150. The elastic member 110 can be fixed to the inner surface 155S of the apex portion 155 of the vane portion 150 via the support member 280.

In the balloon catheter according to the present embodiment, the projection portion 220 has the space portion 270 between the inner surface 20S1 of the balloon 20 and the elastic member 110, and the rigidity member 130 is disposed in the space portion 270. That is, in the balloon catheter according to the present embodiment, dissimilar to the balloon catheter 1 according to Embodiment 1 in which the inside of the projection portion 120 is stuffed with the elastic member 110, no member for stuffing the inside of the projection portion 220 is disposed inside the projection portion 220. Therefore, in the balloon catheter according to the present embodiment, compared to the balloon catheter 1 according to Embodiment 1, the volume of the projection portion 220 in a state where the balloon 20 has deflated can be reduced. Therefore, in the balloon catheter according to the present embodiment, the outer diameter of the balloon 20 in a deflated state can be reduced as much as the volume of the projection portion 220 has decreased in a state where the balloon 20 has deflated. Therefore, in the balloon catheter according to the present embodiment, passing characteristics of the balloon 20 in the biological lumen V in a state where the balloon 20 has deflated can be further improved.

In addition, in the balloon catheter according to the present embodiment, the balloon 20 has the support member 280, which supports the rigidity member 130 inside the balloon 20 when the balloon 20 dilates under the first internal pressure P1. The support member 280 can be disposed between the rigidity member 130 and the elastic member 110. Accordingly, in the balloon catheter according to the present embodiment, when the balloon 20 dilates under the first internal pressure P1, the rigidity member 130 can be pressed to the stenosed site N side by means of the support member 280. Therefore, the balloon catheter according to the present embodiment can more reliably make a nick in the stenosed site N when the balloon 20 dilates under the first internal pressure P1.

In addition, in the balloon catheter according to the present embodiment, the support member 280 has the first region 280A which supports the rigidity member 130 when the balloon 20 dilates under the first internal pressure P1, and the second region 280B which is formed on the center M side of the balloon 20 closer than the first region 280A. In accordance with an exemplary embodiment, the elastic member 110 is disposed in the second region 280B. Accordingly, in the balloon catheter according to the present embodiment, when the balloon 20 dilates under the first internal pressure P1, the rigidity member 130 can be reliably pressed to the stenosed site N side by means of the support member 280 in a state where the support member 280 is restrained by the elastic member 110 from moving in the circumferential direction. Therefore, the balloon catheter according to the present embodiment can reliably make a nick in the stenosed site N when the balloon 20 dilates under the first internal pressure P1.

Figure 12:
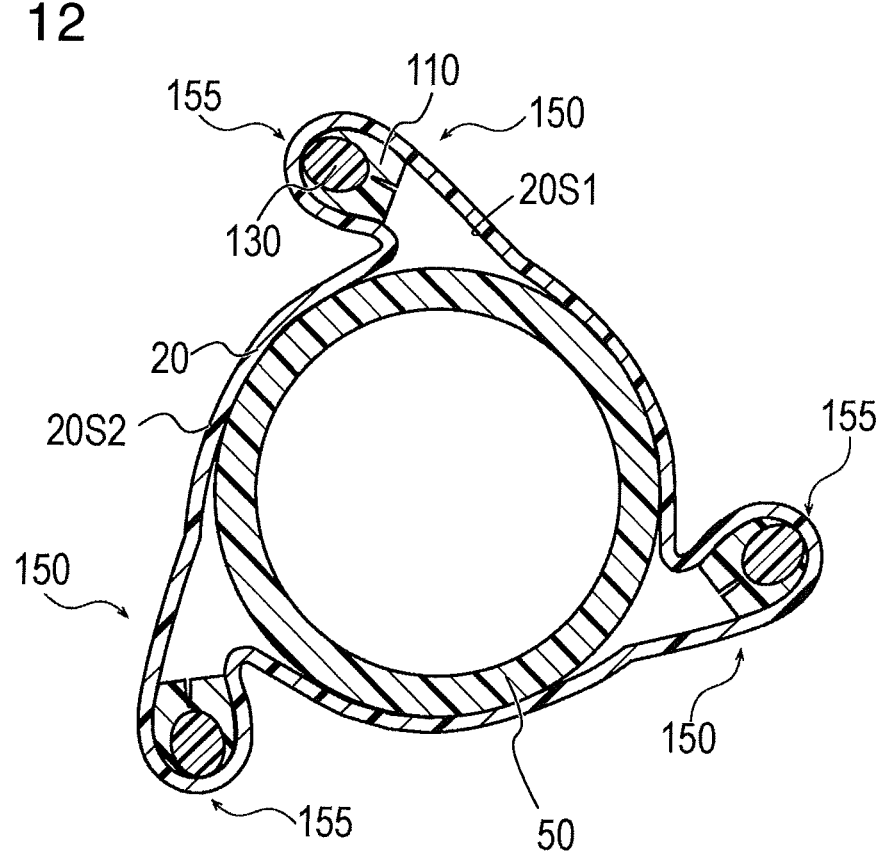
FIG. 12 is a cross-sectional view of a balloon of a balloon catheter according to an alteration example in a deflated state.

In Embodiment 1, the modification example thereof, and Embodiment 2 described above, the apex portion 155 of the vane portion 150 is bent with respect to the radial direction of the shaft 10. However, as illustrated in the example of FIG. 12, the apex portion 155 of the vane portion 150 may be curved with respect to the radial direction of the shaft 10. A balloon catheter according to the present alternative example also exhibits an operational effect similar to those of Embodiment 1, the modification example thereof, and Embodiment 2 described above.

Hereinabove, the balloon catheter has been described through Embodiment 1, the modification example thereof, Embodiment 2, and the alternative example thereof. The present disclosure is not limited to only the configurations described in the embodiments and can be suitably changed based on the disclosed aspects of the disclosure.

For example, in Embodiment 1, the modification example thereof, Embodiment 2, and the alternative example thereof described above, when the balloon dilates under the first internal pressure, the projection portions include the first projection portion, the second projection portion, and the third projection portion which are formed separately at equal intervals in the circumferential direction. However, one projection portion may be disposed in the circumferential direction; or two, four, or more projection portions may be disposed separately in the circumferential direction when the balloon dilates under the first internal pressure.

In addition, in Embodiment 1, the modification example thereof, Embodiment 2, and the alternative example thereof described above, the distal side marker and the proximal side marker of the contrast marker portion are disposed in the shaft at locations corresponding to the intermediate region of the balloon. However, the distal side marker may be disposed at a location corresponding to a distal side inclination region of the balloon such that the end surface of the distal side marker on the proximal side is disposed on the border portion between the distal side inclination region and the intermediate region of the balloon. In addition, the proximal side marker may be disposed at a location corresponding to a proximal side inclination region of the balloon such that the end surface of the proximal side marker on the distal side is disposed on the border portion between the intermediate region and the proximal side inclination region. Note that, the contrast marker portion may be configured to have one marker. In such a case, one marker is disposed at a position in the shaft indicating a substantial center position of the intermediate region of the balloon in the axial direction.

The detailed description above describes a medical elongated body including a dilation member, which is capable of dilating in a biological lumen. The invention is not limited, however, to the precise embodiments and variations described. Various changes, modifications, and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical elongated body comprising:
   a shaft;
   a dilation member configured to be fixed to the shaft on a distal side;
   an elastic member configured to be disposed at a position where portions of an inner surface of the dilation member face each other;
   the dilation member including a projection portion which is a part of the dilation member protruding in a radial direction due to the elastic member disposed at the position where the portions of the inner surface of the dilation member face each other;
   a material of the elastic member is configured to be a material which is further stretched than a material of the dilation member in a circumferential direction when the dilation member dilates;
   when the dilation member dilates under a first internal pressure, a first lumen is formed inside the dilation member, and the projection portion is formed on an outer surface of the dilation member;
   when the dilation member dilates under a second internal pressure, which is higher than the first internal pressure, the elastic member is stretched in the circumferential direction, and the portions of the inner surface of the dilation member are separated from each other due to the elastic member such that the projection portion is not formed on the outer surface of the dilation member, so that a second lumen larger than the first lumen is formed;
   when the dilation member is reduced in pressure to a third internal pressure lower than the second internal pressure, stretching of the elastic member in the circumferential direction is canceled, so that a third lumen smaller than the second lumen is formed and the projection portion is formed again on the outer surface of the dilation member; and
   wherein the elastic member includes a rigidity member, the rigidity member having a rigidity higher than a rigidity of the dilation member and a rigidity of the elastic member.

2. The medical elongated body according to claim 1, wherein the projection portion has a space portion between the inner surface of the dilation member and the elastic member, and the rigidity member is disposed in the space portion.

3. The medical elongated body according to claim 2, wherein when the dilation member dilates under the first internal pressure, the dilation member internally has a support member supporting the rigidity member, and the support member is disposed between the rigidity member and the elastic member.

4. The medical elongated body according to claim 3, wherein the support member has a first region which supports the rigidity member when the dilation member dilates under the first internal pressure, and a second region which is formed on a center side of the dilation member, and the elastic member is disposed in the second region.

5. The medical elongated body according to Claim 1, wherein the rigidity member is fixed to the inner surface of the dilation member.

6. The medical elongated body according to claim 1, wherein the dilation member has an intermediate region which includes a distal end and proximal end, a distal side inclination portion which inclines from the distal end of the intermediate region toward the shaft, and a proximal side inclination portion which inclines from the proximal end of the intermediate region toward the shaft, and the projection portion is formed in the intermediate region.

7. The medical elongated body according to claim 1, wherein the elastic member has a stretch starting portion which is recessed in the radial direction of the shaft when the dilation member dilates under the first internal pressure.

8. The medical elongated body according to claim 1, wherein the dilation member has a plurality of vane portions which are wound around the shaft in a deflated state in which no internal pressure is applied to the inside of the dilation member, and each of the plurality of vane portions includes an apex portion which is curved or bent with respect to the radial direction of the shaft, and the elastic member is disposed on an inner surface of the apex portion of the dilation member.

9. The medical elongated body according to claim 8, wherein the dilation member has an elastic outer surface portion which is disposed on the outer surface of the dilation member;
   a material of the elastic outer surface portion is configured to be a material which is further stretched than the material of the dilation member in the circumferential direction when the dilation member dilate.

10. A medical elongated body comprising:
    a shaft;
    a dilation member configured to be fixed to the shaft on a distal side;
    an elastic member configured to be disposed at a position where portions of an inner surface of the dilation member face each other;
    the dilation member including a projection portion which is a part of the dilation member protruding in a radial direction due to the elastic member disposed at the position where the portions of the inner surface of the dilation member face each other;
    the elastic member being formed of a material which is further stretched than a material of the dilation member in a circumferential direction when the dilation member dilates, and a rigidity member having rigidity higher than rigidity of the dilation member and the elastic member;
    the rigidity member having an elliptical cross-sectional shape perpendicular to an axis of the shaft;

when the dilation member dilates under a first internal pressure, a first lumen is formed inside the dilation member, and the projection portion is formed on an outer surface of the dilation member;

when the dilation member dilates under a second internal pressure higher than the first internal pressure, the elastic member is stretched in the circumferential direction, and the portions of the inner surface of the dilation member are separated from each other due to the elastic member such that the projection portion is not formed on the outer surface of the dilation member, so that a second lumen larger than the first lumen is formed; and wherein when the dilation member is reduced in pressure to a third internal pressure lower than the second internal pressure, stretching of the elastic member in the circumferential direction is canceled, so that a third lumen smaller than the second lumen is formed and the projection portion is formed again on the outer surface of the dilation member.

11. The medical elongated body according to claim 10, wherein the elastic member has the rigidity member having a rigidity higher than a rigidity of the dilation member and a rigidity of the elastic member.

12. The medical elongated body according to claim 10, wherein the projection portion has a space portion between the inner surface of the dilation member and the elastic member, and the rigidity member having rigidity higher than rigidity of the dilation member and the elastic member is disposed in the space portion.

13. The medical elongated body according to claim 12, wherein when the dilation member dilates under the first internal pressure, the dilation member internally has a support member supporting the rigidity member, and the support member is disposed between the rigidity member and the elastic member.

14. The medical elongated body according to claim 13, wherein the support member has a first region which supports the rigidity member when the dilation member dilates under the first internal pressure, and a second region which is formed on a center side of the dilation member, and the elastic member is disposed in the second region.

15. A medical elongated body comprising:
a shaft;
a dilation member configured to be fixed to the shaft on a distal side;
a plurality of elastic members configured to be disposed at positions where portions of an inner surface of the dilation member face each other;
the dilation member including a plurality of projection portions which are a part of the dilation member protruding in a radial direction due to the plurality of elastic members disposed at the positions where the portions of the inner surface of the dilation member face each other;

a material of the plurality of elastic members is configured to be a material which is further stretched than a material of the dilation member in a circumferential direction when the dilation member dilates;

when the dilation member dilates under a first internal pressure, a first lumen is formed inside the dilation member, and the plurality of projection portions are formed separately at equal intervals in the circumferential direction on an outer surface of the dilation member;

when the dilation member dilates under a second internal pressure higher than the first internal pressure, the plurality of elastic members are stretched in the circumferential direction, and the portions of the inner surface of the dilation member are separated from each other due to the plurality of elastic members such that the projection portions are not formed on the outer surface of the dilation member, so that a second lumen larger than the first lumen is formed;

when the dilation member is reduced in pressure to a third internal pressure lower than the second internal pressure, stretching of the plurality of elastic members in the circumferential direction is canceled, so that a third lumen smaller than the second lumen is formed and the projection portions are formed again on the outer surface of the dilation member; and wherein the plurality of elastic members include a rigidity member having a rigidity higher than a rigidity of the dilation member and a rigidity of the plurality of elastic members.

16. The medical elongated body according to claim 15, wherein each of the plurality of projection portions have a space portion between the inner surface of the dilation member and the plurality of elastic members, and the rigidity member having rigidity higher than rigidity of the dilation member and the plurality of elastic members disposed in the space portion.

17. The medical elongated body according to claim 16, wherein when the dilation member dilates under the first internal pressure, the dilation member internally has a support member supporting the rigidity member, and the support member is disposed between the rigidity member and the plurality of elastic members.

18. The medical elongated body according to claim 17, wherein the support member has a first region which supports the rigidity member when the dilation member dilates under the first internal pressure, and a second region which is formed on a center side of the dilation member, and the plurality of elastic members are disposed in the second region.

* * * * *